US010912834B2

(12) United States Patent
Zakrewsky et al.

(10) Patent No.: US 10,912,834 B2
(45) Date of Patent: Feb. 9, 2021

(54) TOPICAL FORMULATIONS BASED ON IONIC SPECIES FOR SKIN TREATMENT

(71) Applicant: The Regents of the University of California, Oakland, CA (US)

(72) Inventors: Michael Zakrewsky, San Diego, CA (US); Samir Mitragotri, Lexington, MA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 43 days.

(21) Appl. No.: 16/329,574

(22) PCT Filed: Aug. 29, 2017

(86) PCT No.: PCT/US2017/049170
§ 371 (c)(1),
(2) Date: Feb. 28, 2019

(87) PCT Pub. No.: WO2018/044920
PCT Pub. Date: Mar. 8, 2018

(65) Prior Publication Data
US 2019/0192661 A1 Jun. 27, 2019

Related U.S. Application Data

(60) Provisional application No. 62/380,761, filed on Aug. 29, 2016.

(51) Int. Cl.
| | | |
|---|---|---|
| *A61K 47/18* | (2017.01) | |
| *A61K 9/00* | (2006.01) | |
| *A61K 47/42* | (2017.01) | |
| *A61K 47/36* | (2006.01) | |
| *A61K 8/41* | (2006.01) | |
| *A61K 8/73* | (2006.01) | |
| *A61K 31/713* | (2006.01) | |
| *A61K 38/38* | (2006.01) | |
| *A61Q 19/08* | (2006.01) | |

(52) U.S. Cl.
CPC ............ *A61K 47/186* (2013.01); *A61K 8/416* (2013.01); *A61K 8/735* (2013.01); *A61K 9/0014* (2013.01); *A61K 31/713* (2013.01); *A61K 38/385* (2013.01); *A61K 47/36* (2013.01); *A61K 47/42* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 4,042,327 A | 8/1977 | Haney | |
| 4,892,737 A | 1/1990 | Bodor | |
| 4,897,355 A | 1/1990 | Eppstein | |
| 5,356,802 A | 10/1994 | Chandrasegaran | |
| 5,487,994 A | 1/1996 | Chandrasegaran | |
| 5,527,675 A | 6/1996 | Coull | |
| 5,539,082 A | 7/1996 | Nielsen | |
| 5,623,049 A | 4/1997 | Loebberding | |
| 5,714,331 A | 2/1998 | Buchardt | |
| 5,736,336 A | 4/1998 | Buchardt | |
| 5,773,571 A | 6/1998 | Nielsen | |
| 5,786,571 A | 7/1998 | Bethel | |
| 5,965,610 A | 10/1999 | Modak | |
| 6,858,217 B2 | 2/2005 | Kerschner | |
| 7,102,000 B2 | 9/2006 | Pfahl | |
| 2006/0110434 A1 | 5/2006 | Yamaguchi | |
| 2007/0003609 A1* | 1/2007 | Collin-Djangone | ... C12N 15/88 424/450 |
| 2009/0317908 A1 | 12/2009 | Haces | |
| 2010/0256174 A1 | 10/2010 | Yamaguchi | |
| 2011/0145940 A1 | 6/2011 | Voytas | |
| 2014/0322307 A1 | 10/2014 | Ferrer Montiel | |
| 2015/0342852 A1 | 12/2015 | Van Den Nest | |
| 2015/0343014 A1* | 12/2015 | Lefevre | ............ A61K 9/06 514/2.3 |
| 2016/0263225 A1 | 9/2016 | Zakrewsky | |

FOREIGN PATENT DOCUMENTS

| | | |
|---|---|---|
| CN | 105434337 | 3/2016 |
| EP | 0747701 | 12/1996 |
| JP | 2008184407 | 4/2008 |
| JP | 2008184402 | 8/2008 |
| WO | 2003055455 | 7/2003 |

(Continued)

OTHER PUBLICATIONS

Abbott, et al., "Design of improved deep eutectic solvents using hole theory", ChemPhysChem, 7(4): p. 803-806 (2006).
Abbott, et al., "Novel solvent properties of choline chloride/urea mixtures", Chem. Commun. (Camb), (1): 70-71 (2003).
Afaq, et al., "Protective effect of pomegranate-derived products on UVB-mediated damage in human reconstituted skin", Exp Dermatol, 18:553-61 (2009).
Am. Chem., "Efficacy of ionic liquids for pathogen neutralization: Turntable solvents as anti-biofilm agents", Abstracts, 39th Northeast Regional meeting of the American Chemical Society, New Haven, Ct., Oct. 23-26, 1 page, (Oct. 25, 2013).
Baker, et al., "Fluorescence studies of protein thermostability in ionic liquids", Chemical Commun (Camb), (8): 940-1 (2004).

(Continued)

*Primary Examiner* — Tracy Vivlemore
(74) *Attorney, Agent, or Firm* — Pabst Patent Group LLP

(57) ABSTRACT

Compositions containing a complex that contains a cation with alkyl chains and a macromolecule anion, and methods of making and using are disclosed. The compositions are typically charge neutral and a liquid at room temperature and standard pressure. The macromolecule anions may be nucleic acids, peptides, proteins, and/or carbohydrates. The compositions have enhanced penetration across the skin barrier (stratum corneum) and into the skin cells, delivering the macromolecules to the skin cells. The compositions are topically applied to the skin and are particularly useful for treatment of skin conditions.

17 Claims, 11 Drawing Sheets

Specification includes a Sequence Listing.

(56) References Cited

FOREIGN PATENT DOCUMENTS

| WO | 2007124397 | 11/2007 |
|---|---|---|
| WO | 2008031105 | 3/2008 |
| WO | 2009066457 | 5/2009 |
| WO | 2011056545 | 5/2011 |
| WO | 2011057209 | 5/2011 |
| WO | 2011072246 | 6/2011 |
| WO | 2015066647 | 5/2015 |

OTHER PUBLICATIONS

Bickers, et al., "The burden of skin diseases: 2004 a joint project of the American Acad Dermatol,he Society for Investigative Dermatology", J Am Academy Derma, 55:490-500 (2006).
Boeckle, and Wagner, "Optimizing targeted gene delivery: chemical modification of viral vectors and synthesis of artificial virus vector systems", AAPS J, 8(4):E731-E742 (2006).
Braasch, et al., "Locked nucleic acid (LNA): fine-tuning the recognition of DNA and RNA", Chem. Biol., 8(1):1-7 (2001).
Brown, et al., "Dermal and transdermal drug delivery systems: current and future prospects", Drug Delivery, 13:175-87 (2006).
Carson, et al., "Antibiofilm activities of 1-alkyl-3-methylimidazolium chloride ionic liquids", Green Chem., 11(4):492-7 (2009).
Cermak, et al, "Efficient design and assembly of custom TALEN and other TAL effector-based constructs for DNA targeting", Nucl. Acids Res., 1-11 (2011).
Chattopadhyay, "Aqueous behavior of Chitosan", International Journal of Polymer Science, 2010:1-7 (2010).
Chen, et al., "Topical delivery of siRNA into skin using SPACE-peptide carriers", J Controlled Release, 179:33-41 (2014).
Chong, et al., "Gene silencing following siRNA delivery to skin via coated steel microneedles: In vitro and in vivo proof-of-concept", J Control Release, 166:211-219 (2013).
Cutler, et al., "Spherical nucleic acids", J Am Chem Soc, 132:1376-91 (2012).
Del Sesto, et al., "Tetraalkylphosphonium-based ionic liquids", J Organometallic Chem., 690(10): 2536-42 (2005).
Dobler, et al., "Ionic liquids as ingredients in topical drug delivery", Int J Pharma, 441((1-2):620-7 (2013).
Earle, et al., "Ionic liquids. Green solvents for the future", Pure App. Chem, 72(7):1391-8 (2000).
Elbashir, et al, "Duplexes of 21-nucleotide RNAs mediate RNA interference in cultured mammalian cells", Nature, 411:494-8 (2001).
Freeman, "A seat at the big table: expanding the role of dermatology at the World Health Organization and beyond", J Invest Dermatol, 134:2663-5 (2014).
Hay, et al., "The global burden of skin disease in 2010: an analysis of the prevalence and impact of skin conditions", J Invest Dermatol, 134:1527-34 (2014).
Hayyan, et al., "Glucose-based deep eutectic solvents: Physical properties", J Mol Liq., 178: 137-41 (2013).
Hough, et al., "The third evolution of ionic liquids: active pharmaceutical ingredients", New J Chem., 31:1429-36 (2007).
Hsu, et al., "Delivery of siRNA and other macromolecules into skin and cells using a peptide enhancer", PNAS, 108:15816-21 (2011).
Hu, "Baculovirus as a highly efficient expression vector in insect and mammalian cells", Acta Pharmacol Sin, 26(4):405-16 (2005).
International Search Report for corresponding PCT/US2017/049170 dated Nov. 13, 2017.
Karande, et al., "Design principles of chemical penetration enhancers for transdermal drug delivery", PNAS, 102:4688-93 (2005).
Karande, et al., "Discovery of transdermal penetration enhancers by high-throughput screening", Nature Biotechnology, 22:192-7 (2004).
Kigasawa, et al., "Noninvasive delivery of siRNA into the epidermis by iontophoresis using an atopic dermatitis-like model rat", Int J Pharm, 383:157-60 (2010).
Kim, et al., "Insertion and Deletion of Mutants of FOKI Restriction Endonuclease" J. Biol. Chem. 269:31, 978-31,982 (1994b).
Kim, et al., "Chimeric restriction endonuclease", PNAS. 91:883-7 (1994a).
Lee, et al., "Enhancement of topical small interfering RNA delivery and expression by low-fluence erbium:YAG laser pretreatment of skin", Hum Gene Therapy, 20:580-8 (2009).
Li, et al., "Alteration of the cleavage distance of Fok I restriction endonuclease by insertion mutagenesis", PNAS, 90:2764-8 (1993).
Li, et al., "Functional domains in Fok I restriction endonuclease.", PNAS, 89:4275-9 (1992).
Lin, et al., "A simple, noninvasive and efficient method for transdermal delivery of siRNA", Arch Dermatol Res, 304:139-44 (2012).
Lovejoy, et al., "Utilization of Metal Halide Species Ambiguity to Develop Amorphous, Stabilized Pharmaceutical Agents as Ionic Liquids" Crystal Growth & Design, 12(11): p. 5357-64 (2012).
MacFarlane, et al., "Pyrrolidinium imides: A new family of molten salts and conductive plastic crystal phases," J Phys Chem., 103(20):4164-70 (1999).
Martin, et al., "Impact of physicochemical properties of engineered fullerenes on key biological responses", Toxicol Appl Pharmacol., 234(1):58-67 (2009).
Meade, et al., "Efficient delivery of RNAi prodrugs containing reversible charge-neutralizing phosphotriester backbone modifications", Nat Biotech, 32:1256-61 (2014).
Miller, et al. "A TALE nuclease architecture for efficient genome editing", Nature Biotechnol., 29:143-8 (2011).
Nishimura, et al., "DNA strands robed with ionic liquid moiety", Biomaterials, 26:5558-63 (2005).
Page, "Heparin and Related Drugs: Beyond Anticoagulant Activity", ISRN Pharmacol, 2013:1-13 doi: 10.1155/2013/910743 (2013).
Palmer, et al., "Molecular techniques to detect biofilm bacteria in long bone nonunion: a case report", Clin Orthop Relat Res,, 469:3037-42 (2011).
Patel, "Recent developments in mushrooms as anti-cancer therapeutics: a review", 3 Biotech, 2:171-85 (2012).
Randeria, et al., "siRNA-based spherical nucleic acids reverse impaired wound healing in diabetic mice by ganglioside GM3 synthase knockdown", PNAS, 112:5573-8 (2015).
Ranke, et al., "Biological effects of imidazolium ionic liquids with varying chain lengths in acute Vibrio fischeri and WST-1 cell viability assays", Ecotoxicol Environ Saf, 58:396-404 (2004).
Ranke, et al., "Lipophilicity parameters for ionic liquid cations and their correlation to in vitro cytotoxicity", Ecotoxicol Environ Saf, 67:430-8 (2007).
Riduan et al., "Imidazolium salts and their polymeric materials for biological applications", Chem. Soc. Rev., 42:9055-70 (2013).
Sheldon, et al., "Use of ionic liquids as 'green' solvents for extractions", Green Chem., 4:147-51 (2002).
Tran, et al., "Noninvasive Drug Delivery Using Ultrasound: Targeting Melanoma Using siRNA Against Mutant (V600E) B-Raf", 8th International Symposium on Therapeutic Ultrasound, 1113(1):423-7 (2009).
Uchida, et al., "Therapeutic effects on atopic dermatitis by anti-RelA short interfering RNA combined with functional peptides Tat and AT1002", J Pharmacol Exp Ther, 388:443-50 (2011).
Ui-Tei, et al, "Sensitive assay of RNA interference in Drosophila and Chinese hamster cultured cells using firefly luciferase gene as target" FEBS Lett, 479:79-82 (2000).
Van Rantwijk,, et al., "Biocatalysis in ionic liquids", Chem. Rev., 107:2757-85 (2007).
Wilkes, et al., "Dialkylimidazolium Chloroaluminate Melts—a New Class of Room-Temperature Ionic Liquids for Electrochemistry, Spectroscopy and Synthesis", Inorg Chem., 21(3):1263-64 (1982).
Yi, et al., "MITF-siRNA formulation is a safe and effective therapy for human melisma", Mol Ther, 19:362-71 (2011).
Yip, et al., "Therapeutic value of glycosaminoglycans in cancer", Mol Cancer Ther, 5:2139-48 (2006).
Yu, et al., "Biodegradable naphthenic acid ionic liquids: synthesis, characterization, and quantitative structure-biodegradation relationship", Chem., 14(35):11174-82 (2008).
Zakrewsky, et al., "Ionic liquids as a class of materials for transdermal delivery and pathogen neutralization", PNAS, 111:13313-8 (2014).

(56) References Cited

OTHER PUBLICATIONS

Zakrewsky, et al., "Nucleic acid delivery into skin for the treatment of skin disease: Proofs-of-concept, potential impact, and remaining challenges", J Contol Rel, 218:445-56 (2015).
Zheng, et al., "Topical delivery of siRNA-based spherical nucleic acid nanoparticle conjugates for gene regulation", PNAS, 109:11975-80 (2012).
Abbott, et al., "Eutectic-Bases Ionic Liquids with Metal-Containing Anions and Cations Chem.", Eur. J., 13:6495-6501 (2007).
Amnuaikit et al., "Skin permeation of propranolol from polymeric film containing terpene enhancers for transdermal use," Int. J. Pharm., 289:167-78 (2005).
Aoyagi, et al., "Formulating propranolol as an amorphous melt affords reduced skin irritation potential for transdermal drug delivery", Technology, 3(4):214-238 (2015).
Cojocaru, et al., "Prodrug ionic liquids: Functionalizing neutral active pharmaceutical ingredients to take advantage of the ionic liquid form," Med Chem Comm., 4:559-63 (2013).
Hori et al.,"Enhancement of propranolol hydrochloride and diazepam skin absorption in vitro: Effect of enhancer lipophilicity," J. Pharm. Sci., 80:32-35 (1991).

Ijiro, et al., "A DNA-Lipid Complex Soluble in organic Solvents", J. Chem. Soc. Chem. Commun., 18:1339-1341 (1992).
International Search Report for PCT application PCT/US2014/063745 dated Apr. 28, 2015.
Kobayashi, et al., "Skin toxicity of propranolol in guinea pigs," J. Toxicol. Sci., 24:103-12 (1999).
Krishna and Pandit, "Transdermal delivery of propranolol" Drug Dev. Ind. Pharm., 20:2459-65 (1994).
Partial European Search Report dated May 29, 2017, in European Patent Application No. 14859243.9.
Pine, et al., "Correlation of plasma propranolol concentration with therapeutic response in patients with angina pectoris," Circulation, 52:886-93 (1975).
Tanaka, et al., "A DNA-Lipid Complex in Organic Media and Formation of an Aligned Cast Film 1", American Chemical Society, 118(44):10680-10683 (1996).
Thacharodi and Rao, "Development and in vitro evaluation of chitosan-based transdermal drug delivery systems for the controlled delivery of propranolol hydrochloride" Biomaterials, 16: 145-8 (1995).

* cited by examiner

TOPICAL FORMULATIONS BASED ON IONIC SPECIES FOR SKIN TREATMENT

CROSS-REFERENCE TO RELATED APPLICATIONS

This application is a National Phase application under 35 U.S.C. § 371 of PCT/US2017/049170, which claims the benefit of and priority to U.S. Ser. No. 62/380,761, filed Aug. 29, 2016, and where permissible are hereby incorporated by reference in their entirety.

STATEMENT REGARDING FEDERALLY SPONSORED RESEARCH

This invention was made with government support under R21 CA191133 awarded by the National Institutes of Health. The government has certain rights in this invention.

REFERENCE TO SEQUENCE LISTING

The Sequence Listing submitted as a text file named "UCSB_2017_042_ST25.txt," created on Aug. 15, 2016, and having a size of 3,132 bytes is hereby incorporated by reference pursuant to 37 C.F.R. § 1.52(e)(5).

FIELD OF THE INVENTION

The field of the invention is transdermal drug delivery formulations, and topically administered formulations, such as for the treatment of skin diseases, and methods for making and using these formulations.

BACKGROUND OF THE INVENTION

Skin disease is one of the most common human illnesses affecting upwards of 70% of the population globally (Hay et al., *Journal of Investigative Dermatology*, 134:1527-1534 (2014)). Symptoms of skin disease range from purely cosmetic (e.g. cellulite, wrinkling, and brown spots) to debilitating and even deadly (e.g. severe pain, skin barrier disruption, dehydration, and systemic infection) (Zakrewsky et al., *Journal of Controlled Release*, 218:445-456 (2015)). High prevalence of skin disease and outward presentation of symptoms combined with high rates of morbidity and mortality associated with severe skin disease results in significant physical, emotional, and economic burden (Hay et al., *Journal of Investigative Dermatology*, 134:1527-1534 (2014); Bickers et al., *Journal of the American Academy of Dermatology*, 55:490-500 (2006)). Skin disease is estimated to be the fourth leading cause of non-fatal disease burden globally, more burdensome than chronic obstructive pulmonary disease, diabetes mellitus, osteoarthritis, and drug abuse (Hay et al., *Journal of Investigative Dermatology*, 134:1527-1534 (2014). However, effective treatment of skin disease remains poorly addressed (Hay et al., *Journal of Investigative Dermatology*, 134:1527-1534 (2014); Bickers et al., *Journal of the American Academy of Dermatology*, 55:490-500 (2006); Freeman E. E., *Journal of Investigative Dermatology*, 134:2663-2665 (2014)).

Topical and transdermal drug delivery provide many advantages over other common delivery routes, such as oral, subcutaneous, and intravenous. These advantages include avoidance of major degradative pathways associated with the gastrointestinal (GI) tract, reduction in side effects associated with systemic toxicity, and needle-free drug administration. Brown, et al., "*Dermal and transdermal drug delivery systems: current and future prospects*", Drug Delivery, 13:175-87 (2006).

Unfortunately, the outermost layer of the skin, the stratum corneum (SC), functions as a barrier to most foreign material and severely limits passive diffusion of many molecules. To overcome this barrier, several strategies have been employed, including the use of chemical penetration enhancers (CPEs). CPEs have been shown to enhance transport through the skin, for a variety of molecules, by disrupting the lipid composition and organization in the SC (Karande, et al., *Proceedings of the National Academy of Sciences of the United States of America*, 102:4688-93 (2005)). However, the extent of lipid disruption often correlates closely with skin irritation (Karande 2005).

For the treatment of bacterial skin infections, a second transport barrier to drug delivery exists—the bacterial biofilm. Biofilm-protected bacteria account for 65% of bacterial infections in humans and are 50-500 times more resistant to antibiotics than unprotected bacteria. Palmer, et al., "*Molecular techniques to detect biofilm bacteria in long bone nonunion: a case report*", Clinical orthopaedics and related research, 469:3037-42 (2011). The antibiotic resistance is due to the transport barrier posed by extracellular polymeric substances (EPS), e.g. polysaccharides, humic acids and nucleic acids. Although the chemical compositions of the SC and bacterial biofilm are different, overcoming the transport barrier posed by the SC and biofilm can be accomplished in a similar manner, such as through fluidization or extraction of the barrier components by a suitable solvent.

For example, extensive efforts have been expended to achieve more effective delivery of topical siRNA. Strategies to overcome the SC barrier include physical methods such as microneedle patches (Chong et al., *Journal of Controlled Release*, 166:211-219 (2013)) and laser ablation (Lee et al., *Human gene therapy*, 20:580-588 (2009)), active methods such as sonophoresis (Tran et al., $8^{th}$ *International Symposium on Therapeutic Ultrasound*, 423-427 (2009)) and iontophoresis (Kigasawa et al., *International journal of pharmaceutics*, 383:157-160 (2010)), and passive methods such as peptides (Hsu et al., *Proceedings of the National Academy of Sciences of the United States of America*, 108:15816-15821 (2011); Lin et al., *Archives of Dermatological Research*, 304:139-144 (2012); Uchida, et al., *Journal of Pharmacology and Experimental Therapeutics*, 388:443-450 (2011); Yi et al., *Molecular Therapy*, 19:362-371 (2011)) and spherical nucleic acids (Randeria et al., *Proceedings of the National Academy of Sciences of the United States of America*, 112:5573-5578 (2015); Zheng et al., *Proceedings of the National Academy of Sciences of the United States of America*, 109:11975-11980 (2012)).

Skin disease symptoms, however, typically manifest over large surface areas and often limit the use of device-based methods. Passive delivery methods are often useful for application on large surface areas; however, current passive methods have limitations including complex synthesis and the necessity to use siRNA conjugation chemistries (Hsu et al., *Proceedings of the National Academy of Sciences of the United States of America*, 108:15816-15821 (2011); Chen et al., *Journal of Controlled Release*, 179:33-41 (2014); Meade et al., *Nat Biotech*, 32:1256-1261 (2014); Cutler et al., *Journal of the American Chemical Society*, 132:1376-1391 (2012)).

There is a need for compositions and methods that improve transdermal transport of therapeutic compositions without irritating the skin.

Therefore, it is an object of the invention to provide compositions for improved transdermal transport of therapeutic, prophylactic, or diagnostic agents.

It is a further object of the invention to provide improved compositions for the treatment of diseases and disorders within the skin.

It is a further object of the invention to provide methods for improving transdermal transport of therapeutic, prophylactic, or diagnostic agents.

It is a still further object of the invention to provide improved methods for treatment of diseases and disorders of the skin.

SUMMARY OF THE INVENTION

Disclosed herein are compositions for improved transdermal transport of therapeutic, prophylactic, or diagnostic agents. The compositions include complexes of macromolecular anions and cations with alkyl chains. The compositions are typically charge neutral, and in liquid form at room temperature and standard pressure. In some aspects, the ratio of macromolecular anions and alkyl chain cations may deviate from 1:1. In this aspect, additional small counterions such as sodium or chloride may be present in a sufficient amount to provide a charge neutral composition.

Suitable macromolecular anions include RNA interference molecules, such as small interfering RNA (siRNA), small hairpin RNA (shRNA), and microRNA (miRNA), peptides, proteins, and/or polysaccharides, such as hyaluronic acid.

Suitable cations with alkyl chains include benzyl dimethyl alkyls, such as benzyl dimethyl octyl ammonium (BDOA), benzyl dimethyl tetradecyl ammonium (BDTA), benzyl dimethyl stearyl ammonium (BDSA). In some embodiments, the cation contains 8 carbons in the alkyl chain, such as benzyl dimethyl octyl ammonium (BDOA) or the cation contains 18 carbons in the alkyl chain, such as benzyl dimethyl stearyl ammonium (BDSA).

Typically, the alkyl chain lengths of cations confer desirable properties to the complexes so that the complexes can transport through the skin barrier (SC) and enter skin cells. The desirable properties include sufficient hydrophobicity, hydrodynamic size, and non-irritating to the skin.

The compositions described herein are suitable for topical administration to the skin without the use of devices to push the composition through the stratum corneum and/or epidermis, modify the porosity of the skin, remove layers from the skin, or pierce the skin, such as microneedle devices, elecroprators or ionoporators. Typically, no additional interventions to the skin, such as injections, sonophoresis, abrasion, electroporation, or ionoporation, are needed to deliver the agent in the compositions through the stratum corneum, optionally to one or more layers of the epidermis.

The compositions described herein are of suitable hydrophobicity to cross the skin barrier and enter skin cells. Preferably the agent is delivered through the epidermis and into the dermis. Optionally, the agent is delivered beyond the dermis.

The compositions are useful for treating one or more conditions of the skin, including cosmetic or disease conditions. Cosmetic conditions include wrinkling, age spots (liver spots), scarring, acne, and the like. Disease conditions include inflammatory, infectious, autoimmune, allergic, neoplastic, and other chronic, acquired or acute diseases of the skin.

BRIEF DESCRIPTION OF THE DRAWINGS

FIG. 2A shows the percent applied dose delivered for the siRNA1. Transdermal delivery of siRNA1 is significantly enhanced when robed with IL moieties. Delivery depth increases from left to right. Naked FAM-siRNA1 (open bars), BDOA-FAM-siRNA1 (hatched bars), BDTA-FAM-siRNA1 (cross-hatched bars), and BDSA-FAM-siRNA1 (closed bars). Error bars represent mean+SD for n=3. * $p<0.05$ compared to naked FAM-siRNA (open bars). FIG. 2B shows the percent applied dose delivered for siRNA2. Delivery depth increases from left to right. Naked FAM-siRNA2 (open bars), BDOA-FAM-siRNA2 (hatched bars), BDTA-FAM-siRNA2 (cross-hatched bars), and BDSA-FAM-siRNA2 (closed bars). Error bars represent mean+SD for n=3. * $p<0.05$ compared to naked siRNA2 (open bars).

FIGS. 3A, 3B, and 3C are line graphs showing percent cell viability relative to control when cells were incubated with the various concentrations of: naked FAM-siRNA1 and robed-FAMsiRNA1s (FIG. 3A), naked FAM-siRNA1 and IL moieties alone (FIG. 3B), or naked FAM-siRNA2 and robed-FAM-siRNA2s (FIG. 3C) after 4 hour incubation. Error bars represent mean+SD for n=6. * $p<0.05$ relative to control (incubated with media alone).

FIG. 4 is a line graph showing percent cell viability relative to control when HEKa cells were incubated with the various concentrations (nM) of BDOA-FAM-siRNA1 for 72 hours. Error bars represent mean+SD for n=6. * $p<0.05$ relative to control (incubated with media alone).

FIG. 5 is a bar graph showing change in GAPDH protein level (GAPDH per total protein (normalized to untreated control)) when HEKa cells were incubated with various formulations of siRNA1, or were left untreated. BDOA-siRNA1 results in significant gene silencing in HEKa cells in vitro. GAPDH expression is relative to control (cells incubated with media alone). Error bars represent mean+SD for n=6. * $p<0.05$ compared to control.

FIG. 6 is a bar graph showing change in percent viability (relative to no UV control) of skin cells treated with various formulations of siRNA. BDOA-siRNA does not cause skin irritation following application to MatTek Epiderm™ tissues. % Viability is normalized by the control (tissue not exposed to UV light). Error bars represent mean+SD for n=3. No statistically significant differences were observed.

FIG. 7A is a bar graph showing change in normalized elastase levels in MatTek Epiderm™ tissues treated with various formulations of siRNA and UV, treated with UV and saline, or untreated (no UV). FIG. 7B is a bar graph showing change in normalized elastin levels in MatTek Epiderm™ tissues treated with various formulations of siRNA and UV, treated with UV and saline, or untreated (no UV). Robed-siRNA significantly limited elastase upregulation and subsequent elastin degradation following MatTek Epiderm® tissue irradiation with UVB light. Elastase expression is normalized by the UV control (tissue exposed to UV light and treated with saline). Elastin expression is normalized by the no UV control (tissue not exposed to UV light). Error bars represent mean+SD for n=3. ** $p<0.01$ compared to UV; saline control. * $p<0.05$ compared to the no UV control.

DETAILED DESCRIPTION OF THE INVENTION

I. Definitions

Figure 1:
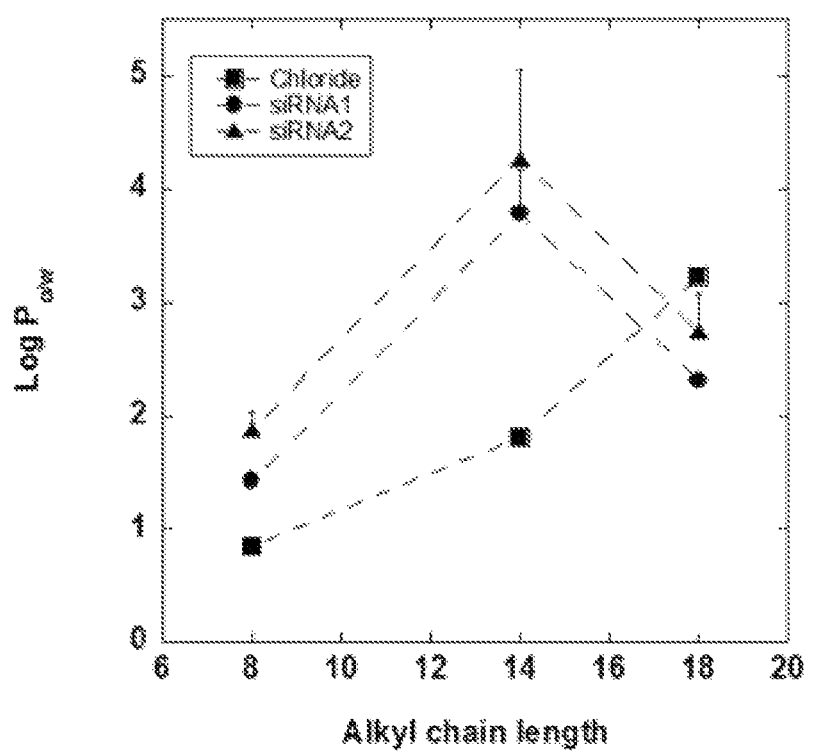
FIG. 1 is a line graph showing a change in octanol-water partitioning coefficient $P_{o/w}$ in log scale (Log $P_{o/w}$) as a function of alkyl chain length for benzyl dimethyl alkyl ammonium chlorides and robed-siRNAs for varying alkyl chain lengths. Error bars represent mean+SD for n=3. Log $P_{o/w}$ for chloride salts are published experimental and predicted values (See Table 2).

The term "alkyl chain" refers to straight-chain, branched-chain and cyclic hydrocarbon groups. Unless specified otherwise, alkyl groups include hydrocarbon groups containing one or more double or triple bonds. An alkyl group containing at least one ring system is a cycloalkyl group. An alkyl group containing at least one double bond is an alkenyl group, and an alkyl group containing at least one triple bond is an alkynyl group.

"Nucleic acids" refer to polymers made from at least two nucleotides. Nucleic acids may be single stranded, as in the case of RNA, or double stranded, as in the case of DNA. Nucleic acids may be made from naturally occurring nucleotides, or may contain one or more non-natural nucleotides. The nucleic acid may also include derivatives and analogs of nucleic acids, including peptide nucleic acids (a polyamino acid sequence substituted by purine and pyrimidine bases) and glycol nucleic acids (wherein the cyclic ribose component is replaced by an acyclic di- or triol linked by phosphodiester bonds).

The term "polysaccharide" refers to a compound made from at least two monosaccharide units which are linked via a glycosylic (or glycosidic) bond. Unless otherwise specified, a polysaccharide may contain only sugar components, or may contain non-sugar components as well, such as amino acids and small molecule aglycones. Polysaccharides having a molecular weight greater than about 10,000 Da may be designated "high-molecular-weight polysaccharides," whereas polysaccharides having a molecular weight less than about 10,000 Da may be designated "low-molecular-weight polysaccharides." Polysaccharide molecular weight may be determined using standard methods known to one skilled in the art, including, but not limited to, mass spectrometry (e.g., of digested fragments by ESI or MALDI) or calculation from known carbohydrate sequences. Polysaccharides can be naturally occurring or non-naturally occurring, synthetic, or semi-synthetic.

The term "protein" refers to a polymer of amino acids linked to each other by peptide bonds to form a polypeptide for which the chain length is sufficient to produce at least a detectable tertiary structure. Proteins having a molecular weight greater than about 100 kDa may be designated "high-molecular-weight proteins," whereas proteins having a molecular weight less than about 100 kDa may be designated "low-molecular-weight proteins." The term "low-molecular-weight protein" excludes small peptides lacking the requisite of at least tertiary structure necessary to be considered a protein. Protein molecular weight may be determined using standard methods known to one skilled in the art, including, but not limited to, mass spectrometry (e.g., ESI, MALDI) or calculation from known amino acid sequences and glycosylation. Proteins can be naturally occurring or non-naturally occurring, synthetic, or semi-synthetic.

"Hydrophilic" refers to substances that have strongly polar groups that readily interact with water. Hydrophilicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in water than in the organic solvent, then the compound is considered hydrophilic. For example, if the organic solvent is octanol, then a negative log P value indicates that the compound is hydrophilic.

"Hydrophobic" refers to substances that lack an affinity for water; tending to repel and not absorb water as well as not dissolve in or mix with water. Hydrophobicity can be quantified by measuring its partition coefficient between water (or a buffered aqueous solution) and a water-immiscible organic solvent, such as octanol, methylene chloride, or methyl tert-butyl ether. If after equilibration a greater concentration of the compound is attained in the organic solvent than in water, the compound is considered hydrophobic. For example, if the organic solvent is octanol, then a positive log P value indicates that the compound is hydrophobic.

The term "effective amount" or "therapeutically effective amount" means a dosage sufficient to treat, inhibit, or alleviate one or more symptoms of a disease state or condition being treated or to otherwise provide a desired pharmacologic and/or physiologic effect. The precise dosage depends on a variety of factors such as subject-dependent variables (e.g., age, immune system health, etc.), the disease or disorder, and the treatment being administered. The effect of the effective amount can be relative to a control. Such controls are known in the art and discussed herein, and can be, for example the condition of the subject prior to or in the absence of administration of the drug, or drug combination, or in the case of drug combinations, the effect of the combination can be compared to the effect of administration of only one of the drugs.

The numerical ranges provided herein are inclusive of all values in a given range. This includes the given minimum value, the given maximum value, as well as values between the minimum value and the maximum value, unless otherwise specified. For numerical ranges referring to integers, the ranges are inclusive of all integers between the minimum value and the maximum value, unless otherwise specified.

Use of the term "about" generally describes values either above or below the stated value in a range of approximately +/−10%; in other aspects the values may range in value either above or below the stated value in a range of approximately +/−5%; in other aspects the values may range in value either above or below the stated value in a range of approximately +/−2%; in other aspects the values may range in value either above or below the stated value in a range of approximately +/−1%. The preceding ranges are intended to be made clear by context, and no further limitation is implied.

II. Composition

The compositions described herein include complexes of macromolecular anions and cations with alkyl chains. The compositions are suitable for topical administration to a subject, such as a human or other mammal. The compositions are typically charge neutral.

Typically, the macromolecular anions and cations within the complex are associated by non-covalent interactions, such as hydrogen bonds, van der Waal's interactions, electrostatic interactions, and stearic arrangement. The complexes form ionic liquid compositions (ILs), certain properties of which are disclosed in the Publication No. WO 2015/066647, the relevant parts of which are incorporated herein by reference.

Macromolecular anions complexed with cations with alkyl chain lengths form compositions, such as ionic liquid compositions. Specific macromolecular anions complexed with cations with alkyl chains are referred to herein as "robed anions", such as robed-siRNA.

A. Ionic Liquids

Ionic liquids (ILs) are crystalline or amorphous salts, zwitterions, or mixtures thereof that are liquids at or near temperatures where most conventional salts are solids. For example, ionic liquids are in the liquid state at a temperature that is less than 200° C., or less than 100° C., or less than 80° C. Some ionic liquids have melting temperatures around room temperature, e.g. between 10° C. and 40° C., or between 15° C. and 35° C.

The ionic liquids are organic salts or mixtures of organic salts which are in a liquid state at room temperature and standard pressure.

Zwitterions are overall neutrally charged molecules, which carry formal positive and negative charges on different chemical groups in the molecule. Examples of ionic liquids are described in Riduan et al., Chem. Soc. Rev., 42:9055-9070, 2013; Rantwijk et al., Chem. Rev., 107:2757-2785, 2007; Earle et al., Pure Appl. Chem., 72(7):1391-1398, 2000; and Sheldon et al., Green Chem., 4:147-151, 2002.

The ionic liquids contain at least one anionic and at least one cationic component. Optionally, the IL contains an additional hydrogen bond donor (i.e. any molecule that can provide an —OH or an —NH group), examples include but are not limited to alcohols, fatty acids, and amines.

The at least one anionic and at least one cationic component may be present in any molar ratio. Exemplary molar ratios (cation:anion) include but are not limited to 1:1, 1:2, 2:1, 1:3, 3:1, 2:3, 3:2, and ranges between these ratios.

In some aspects, the IL composition is a deep eutectic solvent (DES). A DES is composed of a mixture which forms a eutectic with a melting point much lower than either of the individual components in the IL. Exemplary DES include, but are not limited to, choline oleate, choline hexanoate, choline geranate, choline malonate (choline disodium malonate), and urea-choline. In these the formulation is a DES and not a true ionic liquid because excess carboxylate precludes 1:1 ion pairing.

1. Macromolecule Anions

The macromolecule anion in the complex typically has a molecular weight of greater than 500 Da, optionally greater than 750 Da, greater than 800 Da, greater than 900 Da, greater than 1 kDa, or greater than 5 kDa. Optionally the macromolecule anion has a molecular weight that is greater than 10 kDa, greater than 15 kDa, greater than 20 kDa, greater than 30 kDa, greater than 40 kDa. The size of the macromolecule anion is generally less than 500 kDa, 400 kDa, 300 kDa, 100 kDa, optionally less than 50 kDa. For example, the macromolecule anion typically has a molecular weight within the range of 500 Da to 50 kDa, 500 Da to 100 kDa, 500 Da to 300 kDa, 500 Da to 400 kDa, 500 Da to 500 kDa, 750 Da to 50 kDa, 750 Da to 100 kDa, 750 Da to 300 kDa, 750 Da to 400 kDa, 750 Da to 500 kDa, 800 Da to 50 kDa, 800 Da to 100 kDa, 800 Da to 300 kDa, 800 Da to 400 kDa, 800 Da to 500 kDa, 900 Da to 50 kDa, 900 Da to 100 kDa, 900 Da to 300 kDa, 900 Da to 400 kDa, 900 Da to 500 kDa, 1 kDa to 50 kDa, 1 kDa to 100 kDa, 1 kDa to 300 kDa, 1 kDa to 400 kDa, 1 kDa to 500 kDa, 5 kDa to 50 kDa, 5 kDa to 100 kDa, 5 kDa to 300 kDa, 5 kDa to 400 kDa, 5 kDa to 500 kDa, 10 kDa to 50 kDa, 10 kDa to 100 kDa, 10 kDa to 300 kDa, 10 kDa to 400 kDa, 10 kDa to 500 kDa, 15 kDa to 50 kDa, 15 kDa to 100 kDa, 15 kDa to 300 kDa, 15 kDa to 400 kDa, or 15 kDa to 500 kDa.

a. Nucleic Acids

Any nucleic acid for therapeutic, diagnostic, prophylactic, nutraceutical, or drug delivery use can be used in IL compositions. Suitable nucleic acids include complementary DNA (cDNA), DNA aptamers, DNAzymes, RNA aptamers, external guide sequences, RNA interference molecules, such as small interfering RNA, antisense RNA, short hairpin RNA, and micro RNA (miRNA), morpholinos, messenger RNA (mRNA), long non-coding RNA (lncRNA), long intergenic non-coding RNA (lincRNA), as well as ribozymes, and triplex-forming molecules. The nucleic acids are capable of modulating functionality of the genes once they arrive within a cell.

Antisense molecules are designed to interact with a target nucleic acid molecule through either canonical or non-canonical base pairing. The interaction of the antisense molecule and the target molecule is designed to promote the destruction of the target molecule through, for example, RNAse H mediated RNA-DNA hybrid degradation, or, to interrupt a processing function that normally would take place on the target molecule, such as transcription or replication. Preferably, the antisense molecules bind the target molecule with a dissociation constant (Kd) less than or equal to $10^{-6}$, $10^{-8}$, $10^{-10}$, or $10^{-12}$.

Aptamers are small nucleic acids ranging from 15-50 bases in length that fold into defined secondary and tertiary structures, such as stem-loops or G-quartets and are evolved to recognize specific targets. Methods for evolving aptamers to desired targets are known in the art. Optionally, the aptamers bind the target molecule with a Kd less than $10^{-6}$, $10^{-8}$, $10^{-10}$, or $10^{-12}$. Preferably, the aptamer can bind the target molecule with a very high degree of specificity.

Preferred ribozymes cleave RNA or DNA substrates, and more preferably cleave RNA substrates.

Triplex forming nucleic acid molecules interact with either a double-stranded or single-stranded nucleic acid. Preferably, the triplex forming molecules bind a target molecule with a Kd less than $10^{-6}$, $10^{-8}$, $10^{-10}$, or $10^{-12}$.

External guide sequences (EGSs) bind a target nucleic acid molecule forming a complex, which is recognized by RNase P, which then cleaves the target molecule. EGSs can be designed to specifically target a RNA molecule of choice. Methods for making and using EGS molecules to facilitate cleavage of a variety of different target molecules are known in the art.

Gene expression can also be effectively silenced in a highly specific manner through RNA interference (RNAi). Small Interfering RNA (siRNA) is a double-stranded RNA that can induce sequence-specific post-transcriptional gene silencing, thereby decreasing or even inhibiting gene expression. Sequence specific gene silencing can be achieved in mammalian cells using synthetic, short double-stranded RNAs that mimic the siRNAs produced by the enzyme Dicer (Elbashir, et al. *Nature*, 411:494 498 (2001)) (Ui-Tei, et al. *FEBS Lett* 479:79-82 (2000)). siRNA can be chemically or in vitro-synthesized or can be the result of short double-stranded hairpin-like RNAs (shRNAs) that are processed into siRNAs inside the cell. Synthetic siRNAs are generally designed using algorithms and a conventional DNA/RNA synthesizer. Suppliers include AMBION® (Austin, Tex.), CHEMGENES® (Ashland, Mass.), DHARMACON® (Lafayette, Colo.), Glen Research (Sterling, Va.), MWB Biotech (Esbersberg, Germany), PROLIGO® (Boulder, Colo.), and QIAGEN® (Dusseldorf, Germany) siRNA can also be synthesized in vitro using kits such as Ambion's SILENCER® siRNA Construction Kit.

Other useful nucleic acid molecules include CRISPR, zinc finger nucleases (ZFNs), transcription activator-like effector nuclease (TALEN), Locked nucleic acids (LNA), i.e., modified RNA nucleotides (see, for example, Braasch, et al., *Chem. Biol.,* 8(1):1-7 (2001)), Peptide nucleic acids (PNAs).

CRISPR (Clustered Regularly Interspaced Short Palindromic Repeats) is an acronym for DNA loci that contain multiple, short, direct repetitions of base sequences. Methods of preparing compositions for use in genome editing using the CRISPR/Cas systems are described in detail in WO 2013/176772 and WO 2014/018423.

Exemplary ZFN are disclosed for example in U.S. Pat. Nos. 5,356,802; 5,436,150 and 5,487,994; as well as Li et al. *Proc., Natl. Acad. Sci. USA* 89 (1992):4275-4279; Li et al. *Proc. Natl. Acad. Sci. USA,* 90:2764-2768 (1993); Kim et al. *Proc. Natl. Acad. Sci. USA.* 91:883-887 (1994a); Kim et al. *J. Biol. Chem.* 269:31, 978-31,982 (1994b).

TALENs have an overall architecture similar to that of ZFNs, with the main difference that the DNA-binding domain comes from TAL effector proteins, transcription factors from plant pathogenic bacteria. Methods of engineering TAL to bind to specific nucleic acids are described in Cermak, et al, Nucl. Acids Res. 1-11 (2011); US Published Application No. 2011/0145940, and Miller et al. *Nature Biotechnol.,* 29: 143 (2011). General design principles for TALEN binding domains can be found in, for example, WO 2011/072246.

Methods for the chemical assembly of PNAs are known. See, for example, U.S. Pat. Nos. 5,539,082; 5,527,675; 5,623,049; 5,714,331; 5,736,336; 5,773,571; and 5,786,571.

Properties of the morpholino-based subunits typically include: the ability to be linked in an oligomeric form by stable, uncharged backbone linkages; the ability to support a nucleotide base (e.g. adenine, cytosine, guanine, thymidine, uracil or inosine) such that the polymer formed can hybridize with a complementary-base target nucleic acid, including target RNA, with high melting temperature, even with oligomers as short as 10-14 bases; the ability of the oligomer to be actively transported into mammalian cells; and the ability of an oligomer: RNA heteroduplex to resist RNAse degradation.

b. Vectors

Suitable viral vectors include recombinant retroviruses, lentiviruses, adenoviruses, adeno-associated viruses, and baculoviruses. These expression vectors are well known in the art (Boeckle and Wagner, *The AAPS Journal,* 8(4):E731-E742 (2006); Hu, *Acta Pharmacologica Sinica,* 26(4):405-416 (2005)). Bacterial expression vectors including plasmids, cosmids, phagemids, and equivalents thereof, are known in the art and discussed in detail in T. A. Brown. Chapter 2—Vectors for Gene Cloning: Plasmids and Bacteriophages. Gene Cloning and DNA Analysis: An Introduction (6th ed.). (2010) Wiley-Blackwell. ISBN 978-1405181730.

c. Peptides and Proteins

In certain aspects, the macromolecule anion is a peptide or a protein. Suitable peptides or proteins include any peptide or protein that is required or desirable to introduce into a healthy or diseased skin cell. For example, peptides conferring anti-aging, anti-inflammatory, antigenic, antiproliferative, or anti-apoptotic responses to the skin cells may be suitable as macromolecular anions.

Suitable peptides and proteins include structural proteins, such as collagen, enzymes, such as alginase, DNase, RNase, superoxide dismutase, glutathione reductase, lipase, viral antigens, bacterial antigens, fungal antigens, interferons, cytokines, tumor antigens, such as melanoma-associated antigen (MAGE), and the like.

d. Polysaccharides

In certain aspects, the macromolecule anion can be a polysaccharide. The polysaccharide can include neutral, positively charged, or negatively charged monosaccharides units, with the proviso that the polysaccharide has a net negative charge. One or more of the monosaccharide units can be linear or cyclic. The cyclic units can be any combination of an α-anomer or a β-anomer and an L-isomer or a D-isomer. The polysaccharide may be naturally occurring or synthetically derived.

The polysaccharide may have molecular weights between about 1 kDa and about 2,000 kDa, inclusive, between about 1 kDa and about 100 kDa, inclusive, between about 1 kDa and about 50 kDa, inclusive, between about 1 kDa and about 20 kDa, inclusive, between about 3 kDa and about 6 kDa, inclusive, or between about 10 kDa and 20 kDa, inclusive. In some aspects, the polysaccharide may have a molecular weight greater than 500 kDa, greater than 750 kDa, or even greater than 2,000 kDa.

Certain polysaccharides may have a molecular weight between about 500 kDa and about 2,000 kDa, inclusive, between about 500 kDa and about 750 kDa, inclusive, or between about 750 kDa and about 2,000 kDa, inclusive. In other aspects, the polysaccharide can have a molecular weight less than 1,000 Da, preferably between about 300 Da and about 1,000 Da, inclusive.

Preferred carbohydrates include glycosaminoglycans (GAGs), including, but are not limited to, low molecular weight heparins (LMWH), unfractionated heparin (UFH), chondroitins, keratins, and hyaluronic acids (Yip et al., *Molecular Cancer Therapeutics,* 2006, 5:2139-2148).

Other useful polysaccharide include necuparanib (M402, Momenta Pharmaceuticals, Inc.), heparin sulfate or unfractionated heparin (UFH), a low molecular weight heparin (LMWH) such as enoxaparin (LOVENOX®), dalteparin (FRAGMIN®), nadroparin calcium (FRAXIPARIN®), tinzaparin (INNOHEP®), ardeparin (NORMIFLO®), delingoparin, bemiparin, reviparin, or certoparin, or a non-anticoagulanting heparin such as O-desulfated heparin (ODSH), sulodexide, curdlan sulfate, acarbose (GLUCOBAY®), fondaparinux (ARIXTRA®), sodium hyaluronate (ORTHOVISC®), cylexin (CY-1503), rivipansel (GMI-1070), GSC-150, Manα(1-2)Man, sialyl Lewis$^a$, sialyl Lewis$^x$ and their mimetics, GQ1bα and its mimetics, and Lewis$^a$ and its mimetics (Ernst et al., *Nature Reviews Drug Discovery,* 2009, 8:661-77), Sulodexide (SULONEX®, Keryx Biopharmaceuticals).

In other aspects, the polysaccharide may be a plant- or fungal-derived compound, such as a pectin, galactomannan/mannoglycan, xyloglucan, or beta-glucan/lentinan. Other suitable polysaccharides include chitosan, fucoidan, galactan, carrageenan, k-carrageenan, galactofucan, mannoglucoronofucan, arabinogalactans, xylomannan sulfate, xylogalactofucan, ulvan, dextrans and derivatives thereof, and other compounds such as described by Chattopadhyay, *International Journal of Polymer Science,* 2010, 2010:1-7; or Patel, 3 *Biotech,* 2012, 2:171-185).

The polysaccharides, heparin, enoxaparin, dalteparin, nadroparin, tinzaparin, and delingoparin, ODSH, non-antigoagulating heparin, and sulodexide have been tested in clinical trials for efficacy in conditions such as infertility, inhalation injury, inflammation, vulvodynia, ulcerative colitis, diabetic foot ulcers, pregnancy complications, burns, cystic fibrosis, pulmonary conditions, labor, microalbuminuria, and breast, colorectal, lung, prostate, and vasoocclusive cancers, as well as adenocarcinoma of the colon (Page, *ISRN Pharmacology,* 2013, 2013:1-13).

Fucoidan has been noted for antioxidant, immunostimulatory, lipid lowering, antibacterial and antihyperpeisic effects. Fucoidan and ulvan are also used in nanomedicine for wound healing, and for in vitro and in vivo controlled drug release (Patel, 3 Biotech, 2012, 2:171-185).

Galactan, carrageenan and k-carrageenan exhibit antioxidant, immunostimulatory, anti-inflammatory and antinociceptive, anticoagulant and antiviral effects. Galactofucan and mannoglucoronofucan may have antitumor effects. Arabinogalactans may have anticoagulant and antithrombotic effects. Xylomannan sulfate and xylogalactofucan exhibit antiviral effects, particularly against such viruses as influenza, herpes and human immunodeficiency virus (Patel, 3 Biotech, 2012, 2:171-185).

Dextran is a branched polysaccharide. Both dextran and many of its naturally-occurring and synthetic derivatives exhibit antithrombic activity.

A particular group of polysaccharides for topical administration to a subject includes polysaccharides such as alginate, agar, alginic acid (align), carrageen, chitin, chitosan, glucan, carboxymethyl-glucan (CM-glucan), chitin-glucan, carboxymethylcellulose (CMC), dextrins, glycogen, guar gum, gum arabic, honey, hydroxypropyl starch phosphate, hyaluronic acid, hydroxyethyl cellulose, methyl cellulose, mucopolysaccharides (glucosaminoglycans), pectin, sugar tensides, seaweed polysaccharides, fucans, fucoidans, tragant (E 413), xanthan gum, their derivatives, and combinations thereof, preferably hyaluronic acid.

In other aspects, the polysaccharide may be conjugated to an active agent, such as a vaccine, a protein or a small molecule. Exemplary vaccines which may be conjugated to polysaccharides include haemophilus b, pneumococcal, and meningococcal vaccines. Exemplary proteins that may be conjugated to polysaccharides, include trichosanthin, epidermal growth factor, and the anticancer enzymes asparaginase and carboxypeptidase G2. Exemplary small molecule therapeutics that may be conjugated to polysaccharides include doxorubicin, cisplatin, camptothecin, mitomycin, methotrexate, and paclitaxel.

2. Cations

Suitable cations with alkyl chains in the complexes include cationic surfactants. The cationic surfactants have the general formula below:

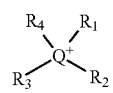

Formula I wherein Q is nitrogen (N) or phosphorus (P), wherein $R_1$, $R_2$, $R_3$, and $R_4$ are independently absent, hydrogen, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, and any pair of $R_1$, $R_2$, $R_3$, and $R_4$ independently combine to form five- and/or six-membered rings, wherein the five- and/or six-membered rings formed from combining any pair of $R_1$, $R_2$, $R_3$, and $R_4$ optionally include an additional heteroatom.

In some aspects, the five- and/or six-membered rings formed from combining any pair of $R_1$, $R_2$, $R_3$, and $R_4$, optionally including an additional heteroatom, can be heterocyclic or heteroaromatic.

In some aspects, the cationic surfactants have the general formula described above for Formula I, with the exception that the cationic surfactant is not cetyltrimethyl ammonium, decyltrimethyl ammonium, benzyldimethyl dodecyl ammonium, myristyltrimethyl ammonium, or dodecyl pyridinium.

In some aspects, the cationic surfactants have the general formula described above for Formula I, and at least one of $R_1$, $R_2$, $R_3$, and $R_4$ is independently a substituted alkyl, wherein the substituted alkyl is a substituted aralkyl or unsubstituted aralkyl.

In some aspects, the cationic surfactants have the general formula described above for Formula I, and at least one of $R_1$, $R_2$, $R_3$, and $R_4$ is independently a substituted alkyl, wherein the substituted alkyl is a substituted aralkyl or unsubstituted aralkyl, and with the exception that the cationic surfactant is not benzyldimethyl dodecyl ammonium.

In some aspects, the cationic surfactants have the general formula described above for Formula I, and $R_1$ is independently a substituted alkyl, wherein the substituted alkyl is a substituted aralkyl or unsubstituted aralkyl, $R_2$, $R_3$, and $R_4$ are independently substituted alkyl or unsubstituted alkyl, with the proviso that when $R_2$, $R_3$, and $R_4$ are substituted alkyl, the substituted alkyl is not a substituted aralkyl or unsubstituted aralkyl.

In some aspects, the cationic surfactants have the general formula described above for Formula I, and $R_1$ is independently a substituted alkyl, wherein the substituted alkyl is a substituted aralkyl or unsubstituted aralkyl, $R_2$, $R_3$, and $R_4$ are independently substituted alkyl or unsubstituted alkyl, with the proviso that when $R_2$, $R_3$, and $R_4$ are a substituted alkyl, the substituted alkyl is not a substituted aralkyl or unsubstituted aralkyl, and with the proviso that the cationic surfactant is not benzyldimethyl dodecyl ammonium.

Any of the cationic surfactants described above can include carbon chains of various lengths, i.e. chain length, as defined by the longest number of contiguously bonded carbon atoms within a chain. The chain length can be between three and twenty carbon atoms, inclusive.

In some aspects, the chain length varies and may be dependent on the overall charge of the macromolecular anion to form a charge neutral, hydrophobic, non-irritating to the skin complex.

In some aspects, the cationic surfactants forming the complexes have the formula shown below:

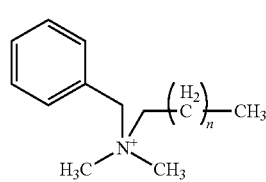

Formula II wherein n is any integer between three and nineteen, including three or nineteen. Examples of cationic surfactants within the scope of Formula II are shown in Tables 4 and 5.

In some aspects, the cationic surfactant in the complex has the formula of Formula II, with the exception that the cationic surfactant is not benzyldimethyldodecyl ammonium.

In some aspects, the cationic surfactant in the complex has the formula of Formula II, where n is 6, 12, or 16. These cationic surfactants are also commonly referred to as benzyldimethyloctyl ammonium, benzyldimethyltetradecyl ammonium, or benzyldimethylstearyl ammonium, respectively.

The lengths of the carbon chains in the cationic surfactant can influence the hydrophobicity of the cation:anion complex, the hydrodynamic size of the cation:anion complex, and the aggregation potency of the complex. For example, Example 1, Tables 2 and 3, and FIG. 1, show that while the anion remains unchanged (siRNA1), the length of the alkyl chain length affects the hydrophobicity, hydrodynamic size, and aggregation properties of the complexes.

It is to be understood that the genera of cationic surfactants or specific cationic surfactants described herein or referred to in the Tables or Examples herein can be specifically included, excluded, or combined in any combination, with the genera of anionic macromolecules or specific anionic macromolecules described herein or referred to in the Tables or Examples herein.

C. Optional Additional Therapeutic, Diagnostic, Prophylactic, and/or Nutraceutic Agents In addition to the complexes described above, the compositions optionally further include one or more additional chemical or biological molecules providing a therapeutic, diagnostic, prophylactic, or nutraceutical effect in vivo. The molecule (also referred to herein as "drug") is selected based on the disease or disorder to be treated or prevented. The drug can be a small molecule or macromolecule, such as a protein or peptide.

A wide range of drugs may be included in the compositions as an additional agent (i.e. in addition to the agent in the complex).

While the composition is generally charge neutral, the additional drug can be positively or negatively charged and contain its own counterion, which can be the same counterion as the one used to neutralize macromolecular ion, or different. Suitable counterions to neutralize the drug include ions suitable for biological applications, such as sodium, calcium, magnesium, chloride, phosphate, sulfate, and others.

Alternatively the additional drug can be charge neutral.

Drugs contemplated for use in the compositions include, but are not limited to, the following categories and examples of drugs and alternative forms of these drugs such as alternative salt forms, free acid forms, free base forms, and hydrates:

analgesics/antipyretics (e.g., aspirin, acetaminophen, ibuprofen, naproxen sodium, buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, diphenhydramine citrate, methotrimeprazine, cinnamedrine hydrochloride, and meprobamate);

antibiotics (e.g., neomycin, streptomycin, chloramphenicol, cephalosporin, ampicillin, penicillin, tetracycline, and ciprofloxacin);

antidiabetics (e.g., biguanides and sulfonylurea derivatives);

antifungal agents (e.g., griseofulvin, ketoconazole, itraconizole, amphotericin B, nystatin, and candicidin);

antihypertensive agents (e.g., propranolol, propafenone, oxyprenolol, nifedipine, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine);

anti-inflammatories (e.g., (non-steroidal) indomethacin, ketoprofen, flurbiprofen, naproxen, ibuprofen, ramifenazone, piroxicam, (steroidal) cortisone, dexamethasone, fluazacort, celecoxib, rofecoxib, hydrocortisone, prednisolone, and prednisone);

antineoplastics (e.g., cyclophosphamide, actinomycin, bleomycin, daunorubicin, doxorubicin, epirubicin, mitomycin, methotrexate, fluorouracil, carboplatin, carmustine (BCNU), methyl-CCNU, cisplatin, etoposide, camptothecin and derivatives thereof, phenesterine, paclitaxel and derivatives thereof, docetaxel and derivatives thereof, vinblastine, vincristine, tamoxifen, and piposulfan);

immunosuppressive agents (e.g., cyclosporine, azathioprine, mizoribine, and FK506 (tacrolimus));

antimigraine agents (e.g., ergotamine, propranolol, isometheptene mucate, and dichloralphenazone);

antianginal agents (e.g., beta-adrenergic blockers; calcium channel blockers such as nifedipine, and diltiazem; and nitrates such as nitroglycerin, isosorbide dinitrate, pentaerythritol tetranitrate, and erythrityl tetranitrate);

antiarthritic agents (e.g., phenylbutazone, sulindac, penicillamine, salsalate, piroxicam, azathioprine, indomethacin, meclofenamate, gold sodium thiomalate, ketoprofen, auranofin, aurothioglucose, and tolmetin sodium);

antigout agents (e.g., colchicine, and allopurinol);

anticoagulants (e.g., heparin, heparin sodium, and warfarin sodium);

thrombolytic agents (e.g., urokinase, streptokinase, and alteplase);

antifibrinolytic agents (e.g., aminocaproic acid);

hemorheologic agents (e.g., pentoxifylline);

antiplatelet agents (e.g., aspirin);

antihistamines/antipruritics (e.g., hydroxyzine, diphenhydramine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, methdilazine, and);

agents useful for calcium regulation (e.g., calcitonin, and parathyroid hormone);

antibacterial agents (e.g., amikacin sulfate, aztreonam, chloramphenicol, chloramphenicol palmitate, ciprofloxacin, clindamycin, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, and colistin sulfate);

antiviral agents (e.g., interferon alpha, beta or gamma, zidovudine, amantadine hydrochloride, ribavirin, and acyclovir);

antimicrobials (e.g., cephalosporins such as cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, and cefuroxime sodium; penicillins such as ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium; erythromycins such as erythromycin ethylsuccinate, erythromycin, erythromycin estolate, erythromycin lactobionate, erythromycin stearate, and erythromycin ethylsuccinate; and tetracyclines such as tetracycline hydrochloride, doxycycline hyclate, and minocycline hydrochloride, azithromycin, clarithromycin);

anti-infectives (e.g., GM-CSF);

steroidal compounds, hormones and hormone analogues (e.g., incretins and incretin mimetics such as GLP-1 and exenatide, androgens such as danazol, testosterone cypionate, fluoxymesterone, ethyltestosterone, testosterone enathate, methyltestosterone, and fluoxymesterone; estrogens such as estradiol, estropipate, and conjugated estrogens; progestins such as methoxyprogesterone acetate, and norethindrone acetate; corticosteroids such as triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate, methylprednisolone sodium succinate, hydrocortisone sodium succinate, triamcinolone hexacetonide, hydrocortisone, hydrocortisone cypionate, prednisolone, fludrocortisone acetate, paramethasone acetate, prednisolone tebutate, and prednisolone acetate; and thyroid hormones such as levothyroxine sodium);

hypoglycemic agents (e.g., human insulin, purified beef insulin, purified pork insulin, recombinantly produced insulin, insulin analogs, glyburide, chlorpropamide, glipizide, tolbutamide, and tolazamide);

hypolipidemic agents (e.g., clofibrate, dextrothyroxine sodium, probucol, pravastitin, atorvastatin, lovastatin, and niacin);

agents useful for erythropoiesis stimulation (e.g., erythropoietin);

oil-soluble vitamins (e.g., vitamins A, D, E, K, and the like); as well as other drugs such as mitotane, halonitrosoureas, anthrocyclines, and ellipticine.

A description of these and other classes of useful drugs and a listing of species within each class can be found in Martindale, *The Extra Pharmacopoeia,* 30*th Ed.* (The Pharmaceutical Press, London 1993), the disclosure of which is incorporated herein by reference in its entirety.

D. Exemplary Complexes

The anions and cations described above can be combined to form the IL. For example, the nucleic acids, vectors, anionic peptide or protein, anionic polysaccharide, and combinations thereof, can be combined with the cations of Formula I. Exemplary complexes include:

(i) Exemplary Complexes of siRNA and Cation Surfactants

In some forms, the IL contains an siRNA in complex with a cation surfactant of Formula I, as described above, (i) with the exception that the cationic surfactant is not cetyltrimethyl ammonium, decyltrimethyl ammonium, benzyldimethyldodecyl ammonium, myristyltrimethyl ammonium, or dodecyl pyridinium; (ii) at least one of $R_1$, $R_2$, $R_3$, and $R_4$ is independently a substituted alkyl, wherein the substituted alkyl is a substituted aralkyl or unsubstituted aralkyl; (iii) at least one of $R_1$, $R_2$, $R_3$, and $R_4$ is independently a substituted alkyl, wherein the substituted alkyl is a substituted aralkyl or unsubstituted aralkyl, and wherein the cationic surfactant is not benzyldimethyl dodecyl ammonium; (iv) $R_1$ is independently a substituted alkyl, wherein the substituted alkyl is a substituted aralkyl or unsubstituted aralkyl, $R_2$, $R_3$, and $R_4$ are independently substituted alkyl or unsubstituted alkyl, with the proviso that when $R_2$, $R_3$, and $R_4$ are substituted alkyl, the substituted alkyl is not a substituted aralkyl or unsubstituted aralkyl; or (iv) $R_1$ is independently a substituted alkyl, wherein the substituted alkyl is a substituted aralkyl or unsubstituted aralkyl, $R_2$, $R_3$, and $R_4$ are independently substituted alkyl or unsubstituted alkyl, with the proviso that when $R_2$, $R_3$, and $R_4$ are substituted alkyl, the substituted alkyl is not a substituted aralkyl or unsubstituted aralkyl, and wherein the cationic surfactant is not benzyldimethyl dodecyl ammonium.

In some forms, the IL contains an siRNA in complex with a cationic surfactant of Formula II

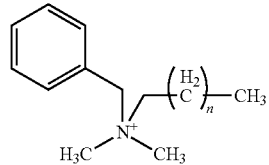

Formula II wherein n is any integer between three and nineteen, including three or nineteen the exception that the cationic surfactant is not benzyldimethyldodecyl ammonium, wherein the siRNA is selected from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In some forms, the IL contains an siRNA in complex with a cationic surfactant selected from hydroxyethyltrimethyl ammonium, tetradecyltrimethyl ammonium, benzyldimethyltetradecyl ammonium, benzyldimethylstearyl ammonium, and combinations thereof, wherein the siRNA is selected from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

In some forms, the IL contains an siRNA in complex with a cationic surfactant selected from benzyldimethyltetradecyl ammonium, benzyldimethylstearyl ammonium, and combinations thereof, whrein the siRNA is selected from SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, and combinations thereof.

(ii) Exemplary Complexes of Anionic Polysaccharides and Cationic Surfactants

In some forms, the IL contains an anionic polysaccharide in complex with a cation surfactant of Formula I.

In some forms, the IL contains an anionic polysaccharide (e.g. hyaluronic acid, alginate, alginic acid, glycosaminoglycans, etc.) in complex with a cation surfactant of Formula I as described above, with the exception that (i) the cationic surfactant is not cetyltrimethyl ammonium, decyltrimethyl ammonium, benzyldimethyldodecyl ammonium, myristyltrimethyl ammonium, or dodecyl pyridinium; (ii) at least one of $R_1$, $R_2$, $R_3$, and $R_4$ is independently a substituted alkyl, wherein the substituted alkyl is a substituted aralkyl or unsubstituted aralkyl; (iii) at least one of $R_1$, $R_2$, $R_3$, and $R_4$ is independently a substituted alkyl, wherein the substituted alkyl is a substituted aralkyl or unsubstituted aralkyl, and wherein the cationic surfactant is not benzyldimethyl dodecyl ammonium; (iv) $R_1$ is independently a substituted alkyl, wherein the substituted alkyl is a substituted aralkyl or unsubstituted aralkyl, $R_2$, $R_3$, and $R_4$ are independently substituted alkyl or unsubstituted alkyl, with the proviso that when $R_2$, $R_3$, and $R_4$ are substituted alkyl, the substituted alkyl is not a substituted aralkyl or unsubstituted aralkyl; or (iv) $R_1$ is independently a substituted alkyl, wherein the substituted alkyl is a substituted aralkyl or unsubstituted aralkyl, $R_2$, $R_3$, and $R_4$ are independently substituted alkyl or unsubstituted alkyl, with the proviso that when $R_2$, $R_3$, and $R_4$ are substituted alkyl, the substituted alkyl is not a substituted aralkyl or unsubstituted aralkyl, and wherein the cationic surfactant is not benzyldimethyl dodecyl ammonium.

In some forms, the IL contains hyaluronic acid, alginate, alginic acid, glycosaminoglycans, and combinations thereof, preferably hyaluronic acid, in complex with a cationic surfactant of Formula II

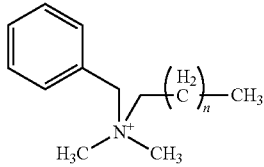

Formula II wherein n is any integer between three and nineteen, including three or nineteen the exception that the cationic surfactant is not benzyldimethyldodecyl ammonium.

In some forms, the IL contains hyaluronic acid, alginate, alginic acid, glycosaminoglycans, and combinations thereof, preferably hyaluronic acid, in complex with a cationic surfactant selected from hydroxyethyltrimethyl ammonium, tetradecyltrimethyl ammonium, benzyldimethyltetradecyl ammonium, benzyldimethylstearyl ammonium, and combinations thereof.

In some forms, the IL contains hyaluronic acid in complex with a cationic surfactant selected from hydroxyethyltrimethyl ammonium, tetradecyltrimethyl ammonium, benzyldimethyltetradecyl ammonium, benzyldimethylstearyl ammonium, and combinations thereof.

E. Properties of the Compositions

The cations and the macromolecular anions form complexes that typically are charge neutral, sufficiently hydrophobic to cross the skin barrier and enter skin cells. Additionally, the compositions are generally non-irritating to the skin.

1. Charge Neutrality

Typically, the compositions are charge neutral.

In the complexes included in the compositions, the cations, which can contain various alkyl chain lengths, and the macromolecular anions, are typically mixed at 1:1 charge ratio. However, other charge ratios may be used to mix the cations of various alkyl chain lengths and the macromolecular anions, for example, suitable charge ratios (charges on the macromolecular anions to the charges on the alkyl chain cations) include 0.5:1, 1:1, or 2:1, and ratios there between. In some aspects, the cations of various alkyl chain lengths and the macromolecular anions are mixed at a molar ratios of 1:1, 1:2, 1:3, 1:4, 1:5, 1:6, 1:7, 1:8, 1:9, 1:10, 2:1, 3:1, 4:1, 5:1, 6:1, 7:1, 8:1, 9:1, or 10:1, or any suitable molar ratio to confer charge neutrality to the overall complex. When the ratio of charges on the macromolecular anions to the charges on the alkyl chain cations deviates from one (1:1), additional counterions may be present in a sufficient amount to neutralize the charges on the complex. Suitable counterions to neutralize the drug include ions suitable for biological applications, such as sodium, calcium, magnesium, chloride, phosphate, sulfate, and others.

The charge neutrality of the composition may be conferred by inclusion of other ions in addition to those in the complex. For example, the macromolecular ion complex can be suspended or dissolved in a buffer, such as a phosphate buffered saline.

2. Hydrophobicity of Complexes in Composition

The hydrophobicity of the formed complexes may be characterized by the octanol/water partition coefficient ($P_{o/w}$), presented in $Log_{10}$ values (Table 2). Typically, the hydrophobicity of the complex of a cation with varying alkyl chain lengths and a macromolecular anion, as determined by its octanol/water partition coefficient ($P_{o/w}$), is greater by at least one Log(10) unit (Log $P_{o/w}$) compared to the hydrophobicity of the macromolecule anion when it is complexed with sodium ion.

In some aspects, the hydrophobicity of the macromolecule anion, as determined by its octanol/water partition coefficient, is increased by a factor ranging from one to five Log(10) units (Log $P_{o/w}$).

To determine the hydrophobicity of a given macromolecular anion in a complex, the Log $P_{o/w}$ for the macromolecular anion when in the complex of interest can be determined and compared to the Log $P_{o/w}$ for the same macromolecular anion when complexed to a sodium ion. The $P_{o/w}$ partition coefficient may be measured using any standard test. An exemplary test is provided below.

5 mL $ddH_2O$ may be mixed overnight at room temperature with 5 mL octanol. A complex containing a macromolecular anion complexed with sodium ions or with cations with alkyl chains is then added to the mixture and again allowed to mix overnight at room temperature in the dark. After overnight incubation, the solution is centrifuged to separate the octanol layer and water layer. The concentration of the macromolecular anion present in each layer is quantified by UV-Vis spectroscopy, or fluorescence spectroscopy, using, for example, a SAFIRE, XFLUOR4, V4.50 microplate reader (Tecan Group Ltd, Morrisville, N.Y.). For detection of siRNA, the fluorescence detection may be performed at an excitation of 485 nm and an emission of 520 nm, and the method may be validated for linearity, accuracy, and precision. Log $P_{o/w}$ may be calculated as the logarithm of the ratio of fluorescence in the octanol layer compared to the water layer.

3. Non-Irritating to the Skin

The compositions described herein are typically non-irritating to the skin. Each of the components in the IL (i.e., anionic and cationic components) may on its own be irritating to the skin. However, the combination of the ionic components used in the complex that is included in the composition is not irritating, or substantially non-irritating (i.e. causes at most a minimal skin reaction) when applied to the surface of the skin.

The compositions may cause minimal or no skin reaction, such as redness, rash, inching, burning or tingling sensations. Minimal skin reaction may be understood as slight skin reaction with signs of irritation but one that is not uncomfortable or painful to the subject.

For example, the compositions are non-irritating to the skin even when either or both the macromolecule anion and the cation alone are irritating to the skin.

Typically, the compositions are non-toxic to the skin cells. The compositions do not induce any adverse reactions in the healthy skin cells, such as reduction in viability of healthy skin cell, when applied to the skin. For example, the compositions have substantially the same cytotoxicity to the healthy skin cells in vitro or in vivo as the cytotoxicity in vitro or in vivo of the macromolecule anion complexed with a sodium cation.

4. Transport Through the Skin Layers

Typically, the compositions are sufficiently hydrophobic to transport through one or more the skin barrier layers, such as SC, and/or through one or more skin cell layers, such as epidermis and dermis without the need for an additional treatment of the skin to increase its porosity, or to push the compositions through the SC and/or one or more additional layers of the skin.

The human skin can be divided into epidermis and dermis. Each of these components is subdivided into layers.

a. Transport Through the Epidermis

The epidermis is divided into five sublayers: stratum corneum, stratum lucidum, stratum granulosum, stratum spinosum, and stratum germinativum (also called "stratum basale"). The epidermis is devoid of blood vessels and is nourished by diffusion from the dermis.

The epidermis is divided into several layers of cells that are formed through mitosis at the innermost layers. They move up the strata changing shape and composition as they differentiate and become filled with keratin. They eventually reach the top layer called stratum corneum, which serves as a skin barrier layer, and are sloughed off, or desquamated. The outermost layer of the epidermis consists of 25 to 30 layers of dead cells.

The complexes described herein are able to transport through the five different sublayers of the epidermis and reach the dermis. Typically, after topical application to the skin, the macromolecular anions complexed with the cations with alkyl chains are transported through the stratum corneum and reach the various sublayers of epidermis, in greater amounts than the amounts achieved following topical application of the same macromolecular anions when complexed with sodium ions. The macromolecular anions complexed with the cations with alkyl chains may pass through one or more layers of the skin, such as one or more layers of the epidermis, and even through one or more layers of the dermis, following topical administration. In these aspects, the composition passes through the one or more layers of the skin in greater amounts than the amounts achieved following topical application of the same macromolecular anions when complexed with sodium ions.

Optionally the macromolecular anions complexed with the cations with alkyl chains pass through all of the layers of the skin, following topical administration. In this aspect, the composition passes through all the layers of the skin in greater amounts than the amounts achieved following topical application of the same macromolecular anions when complexed with sodium ions.

b. Transport Into the Dermis

The dermis is the layer of skin beneath the epidermis that consists of epithelial tissue. The dermis is structurally divided into two areas: a superficial area adjacent to the epidermis, called the papillary region, and a deep thicker area known as the reticular region.

The dermis is tightly connected to the epidermis by a basement membrane. It also harbors many nerve endings that provide the sense of touch and heat. It contains the hair follicles, sweat glands, sebaceous glands, apocrine glands, lymphatic vessels and blood vessels. The blood vessels in the dermis provide nourishment and waste removal from its own cells as well as from the stratum basale of the epidermis.

Preferably, after topical application of the composition to the skin, the macromolecular anions complexed with the cations with alkyl chains are transported through the epidermis and into one or more layers of the dermis, in greater amounts than the amounts achieved following topical application of the same macromolecular anions complexed with sodium ions.

III. Methods of Making the Composition

Methods of making the compositions are known in the art and described by Nishimura et al., *Biomaterials,* 26:5558-5563 (2005).

Typically, the methods include chloride salts of the cations and converting these to their corresponding hydroxide salts, such as by using an anion exchange resin (e.g., Amberlite IRA-402 hydroxide form anion exchange resin from Santa Cruz Biotechnology, Dallas, Tex.), as indicated in Scheme 1. The chloride salts of the cations are dissolved in ultrapure ddH$_2$O (e.g., ultrapure ddH$_2$O from Life Technologies, Grand Island, N.Y.) at a suitable concentration, such as a concentration of 1.0% wt, and mixed with excess resin for 1 hour under constant agitation. The slurry is then centrifuged to pellet the resin and collect supernatant. Complete anion exchange can be verified by the lack of precipitate following dropwise addition of silver nitrate (e.g., 2 g/mL solution of silver nitrate in ddH$_2$O from Sigma Aldrich, St. Louis, Mo.). The final solution of the cation hydroxide can be freeze-dried to remove ddH$_2$O.

Scheme 1

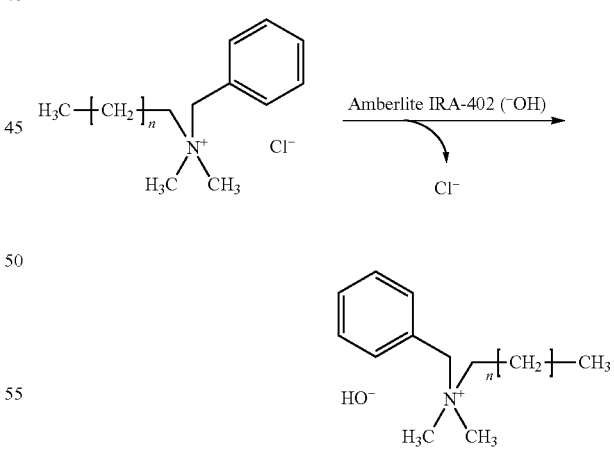

Similarly, the macromolecular anion sodium salts can be converted to acidic form using a cation exchange resin (e.g., Amberlite IR-120 hydrogen cation exchange resin from Santa Cruz Biotechnology, Dallas, Tex.), as indicated in Scheme 2. Complete cation exchange can be verified by titration. The final solution of hydrogen form of macromolecular anion can be freeze-dried to remove ddH$_2$O.

Scheme 2

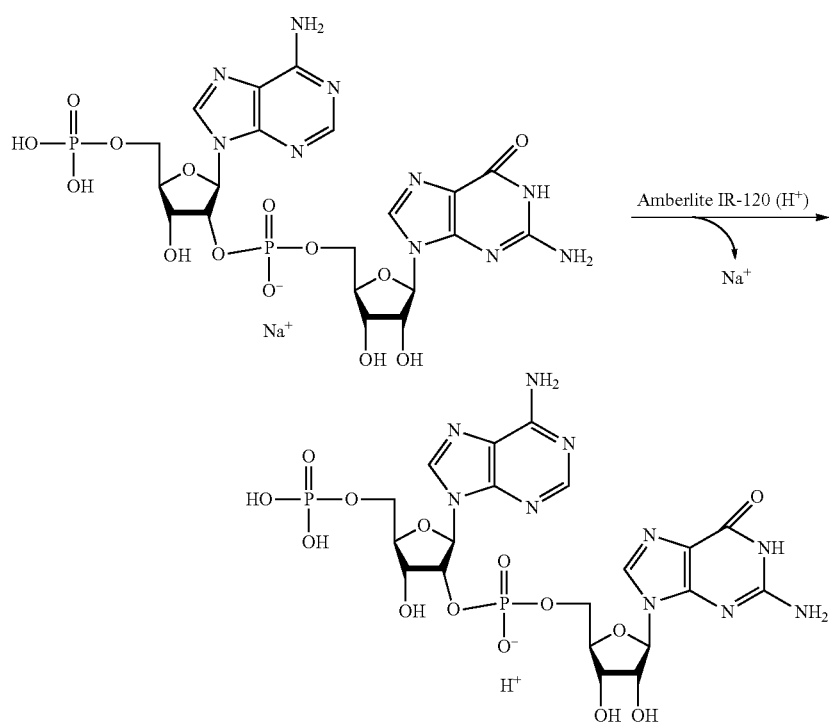

Acidic groups on the macromolecular anion can be complexed, optionally neutralized, to the corresponding cation by addition of cation in a suitable solvent (e.g., the hydroxide form of the cation, optionally a cationic surfactant, in methanol), as shown in Scheme 3. Neutralization is allowed to proceed for a suitable period of time, such as overnight, at room temperature with constant agitation. The solvent (e.g. methanol) is then removed, such as by rotary evaporation, and subsequently freeze-dried, and robed-anion is stored, e.g. at −20° C., until further use.

Scheme 3

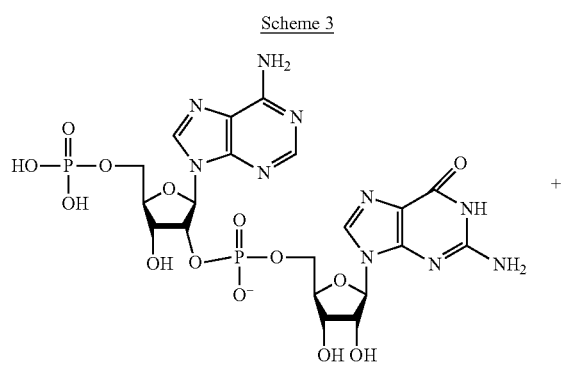

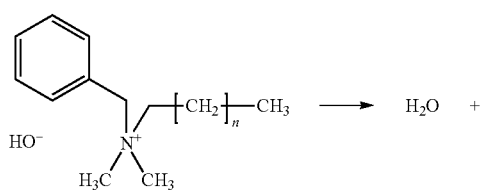

-continued

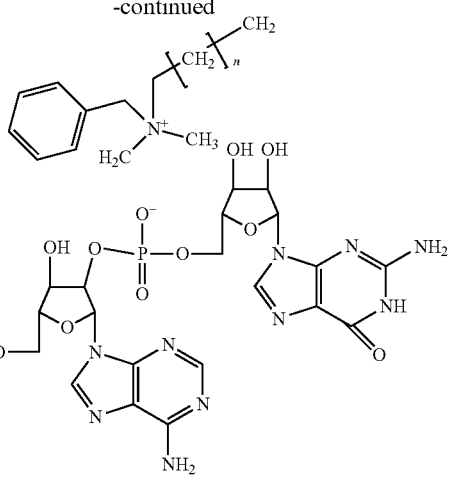

IV. Methods of Using the Composition

The compositions are applied topically to a subject's (human or other mammal) skin in an effective amount to transport the complex through the stratum corneum, and preferably to or through one or more layers of the epidermis. An effective amount of the complex may be transported to the dermis. Optionally, the complex is delivered to cells beyond one or more layers of the dermis. The complex may be transported through the various layers of the skin alone, or in combination with one or more with additional therapeutic, diagnostic, prophylactic, or nutraceutical agents.

The complex is transported through the stratum corneum, and optionally to or through the different layers of the epidermis and/or dermis without additional treatments to the skin to increase the porosity of the skin, to remove one or more layers of the stratum corneum, and/or to push the complex or components of the composition through the skin, prior to, simultaneous with, or subsequent to, topical application of the composition.

When applied to an individual's skin, the compositions do not cause undue irritation, such as evidenced by redness, burning and/or itching sensations.

Each of the components in the IL complexes (i.e., anionic and cationic components), or ionic component(s) in the IL and drug, may on its own be irritating to the skin. However, the combination of the ionic components (or ionic component and drug) used in the composition is not irritating when applied to the surface of the skin.

The compositions described herein may be topically applied in an effective amount to treat skin disease. In some embodiments, the compositions contain, RNAi molecules, such as siRNA. Optionally, the composition contains a complex, such as BDOA-siRNA.

A. Targeted Delivery

The compositions may be selected to deliver a drug to a particular site, such as within the stratum corneum, epidermis and/or dermis, or through and beyond all of the layers of the skin.

As shown in the examples, different ILs demonstrated three different transport regimes, depending on the IL employed: 1) Drug retention in the donor solution. 2) Enhanced localization and retention within the SC, epidermis, and dermis. 3) Enhanced transdermal penetration through all layers of the skin and into the acceptor solution. In all of the aspects, the composition is not irritating to the skin, although one or more of the components on its own may be irritating.

In some aspects, the components of the composition (e.g. cationic component, anionic component) are selected such that the agent (or complex) to be delivered is delivered within the layers of the skin. This may be particularly useful for the treatment of diseases or disorders of the skin, such as treatment of an infection, cut, burn, or rash.

In other aspects, the components of the composition (e.g. cationic component, anionic component, and/or drug) are selected such that the drug to be delivered is transported through the skin, such as beyond the layers in the dermis.

In still other aspects, the components of the composition may be selected such that they prevent transfer of a drug (or other substance) through the stratum corneum. This may be useful as a coating to protect the skin or treat large open wounds Suitable complexes for use in these compositions possess characteristics that limit their penetration. These characteristics include formation of aggregates or particles, increased viscosity, and/or increased density, compared to compositions that pass through the stratum corneum.

B. Conditions to be Treated

The IL compositions described herein may be used for transdermal macromolecular anion delivery, optionally with therapeutic, diagnostic, prophylactic, and/or nutraceutical drugs.

The IL compositions may be applied to the surface of the skin to treat a disease or disorder of the skin, including but not limited to atopic dermatitis, acne, wound, rash, folliculitis, furunculosis, carbunculosis fungal infection, and other diseases of infectious origin.

C. Effective Amounts

Effective amounts vary with condition to be treated and the macromolecular anion and, optionally, additional drug to be delivered to the skin. The effective amount may be reached with one, or more than one topical application of the compositions. For example, each application containing 10 ng, 20 ng, 50 ng, 100 ng, 1 μg, 10 μg, 20 μg, 50 μg, 100 μg, or 10 mg of one or more agents (macromolecular anion, optionally with an additional drug), may be applied to a skin site and deliver an effective dose of 10 ng, 20 ng, 50 ng, 100 ng, 1 μg, 10 μg, 20 μg, 50 μg, 100 μg, 1 mg, 10 mg, 20 mg, 50 mg, or 100 mg of the agent(s), respectively.

An effective dose of an active agent may be delivered by altering the number of applications, by altering the amount of the agent in each of the applications, or both. The effective amount of the active agent may be delivered over a period of 1 day, 2-3 days, or over the period of one week, or few weeks to 3-6 months.

Suitable dosages include topical applications of the compositions in suitable volumes that contain between 0.001 μg to 1000 mg of the macromolecule anion and/or drug to the skin site of the subject to be treated.

D. Dosage Forms

The IL compositions may be in dosage units and dosage forms delivering an effective amount of the macromolecular anion and/or drug to the skin.

Any dosage form suitable for delivery to the skin may be used. The compositions may be in the form of films, depots, patches or neat liquids, creams, lotions. The dosage forms may be prepackaged for delivery of the effective amount of the macromolecular anion via single, or multiple applications.

In one aspect, compositions are delivered to the skin surface by a drug delivery device containing a reservoir for holding the compositions. Optionally, the reservoir also contains one or more additional drug(s).

In another aspect, the compositions may be contained within a drug delivery device. A variety of different devices having different geometries and structures may be used. For example, the device may be a multicompartment device, which contains the IL compositions, optionally, additional compartments contain one or more additional agents.

Typically, the dosage forms are delivered without the need of injecting devices, such as devices with microneedles, or other devices or agents for increasing skin permeability or pushing the complexes through the skin, as the IL compositions are able to cross the skin barrier and reach the cells of the skin.

EXAMPLES

Example 1. Synthesis and Characterization of Robed-siRNAs

Materials and Methods siRNA robed with ionic liquid (IL) moieties were synthesized by acid-base neutralization as described previously (Nishimura et al., *Biomaterials,* 26:5558-5563 (2005)). Benzyl dimethyl alkyl ammonium chloride salts were purchased from Sigma Aldrich (St. Louis, Mo.). FAM-GAPDH siRNA (siRNA1, 5'-FAM-GACGUAAACGGCCACAAG UUC-3' (SEQ ID NO:1)), FAM-GAPDH siRNA (siRNA2, 5'-FAM-GUGUGAACCACGAGAAAUAUU-3'(SEQ ID NO:2)), FAM-Elastase siRNA (siRNA3, 5'-FAM-UCACUUACAG-GAUCUAUAAUU-3' (SEQ ID NO:3)), and FAM-Control siRNA (siRNA4, 5'-FAM-UAAGGCUAUGAAGAGAUA-CUU-3' (SEQ ID NO:4)) were purchased from Dharmacon, Thermo Fisher Scientific (Waltham, Mass.).

Chloride salts were converted to their corresponding hydroxide salts using Amberlite IRA-402 hydroxide form anion exchange resin (Santa Cruz Biotechnology, Dallas, Tex.). Benzyldimethyl alkyl ammonium chloride salts were dissolved in ultrapure ddH$_2$O (Life Technologies, Grand Island, N.Y.) at a concentration of 1.0% wt and mixed with excess resin for 1 hour under constant agitation. The slurry was then centrifuged to pellet the resin and collect supernatant. Complete anion exchange was verified by the lack of precipitate following dropwise addition of silver nitrate (2 g/mL in ddH2O, Sigma Aldrich, St. Louis, Mo.). The final solution of benzyldimethyl alkyl ammonium hydroxide was freeze-dried to remove ddH2O. Similarly, siRNA sodium salts were converted to acidic form using Amberlite IR-120 hydrogen cation exchange resin (Santa Cruz Biotechnology, Dallas, Tex.). Complete cation exchange was verified by titration. The final solution of hydrogen form of siRNA was freeze-dried to remove ddH$_2$O. Acidic groups on siRNA were neutralized by addition of equivalent benzyl dimethyl alkyl ammonium hydroxide in methanol. Neutralization was allowed to proceed overnight at room temperature with constant agitation. Methanol was then removed by rotary evaporation and subsequent freeze-drying, and robed-siRNA was stored at −20° C. until further use.

Composition of robed-siRNA was confirmed by elemental analysis. CHN elemental analysis was performed with a CE-440 Rapid Analysis Elemental Analyzer (Exeter Analytical, North Chelmsford, Mass.). Sample size was ~1 mg weighed in small aluminum capsules. Capsules were placed in protective nickel sleeves, loaded into the autosampler wheel, and introduced into the combustion furnace by means of a mechanically operated quartz ladle. Percent weights of carbon, nitrogen, and hydrogen were determined by high-temperature combustion at 1000° C. in an oxygen-enriched helium atmosphere.

Robed-siRNA were characterized by measuring partitioning into octanol and water (Log $P_{o/w}$). 5 mL ddH$_2$O was mixed overnight at room temperature with 5 mL octanol. FAM-siRNA or robed-FAM-siRNA was then added to the mixture and again allowed to mix overnight at room temperature in the dark. After overnight incubation, the solution was centrifuged to separate the octanol layer and water layer. The concentration of FAM-siRNA present in each layer was quantified by fluorescence spectroscopy using a SAFIRE, XFLUOR4, V4.50 microplate reader (Tecan Group Ltd, Morrisville, N.Y.). Fluorescence detection was performed at an excitation of 485 nm and an emission of 520 nm, and the method was validated for linearity, accuracy, and precision. The linear range during the measurements was from 0.25 pmol/mL to 25 pmol/mL ($r^2$=0.9999). Log $P_{o/w}$ was calculated as the logarithm of the ratio of fluorescence in the octanol layer compared to the water layer.

Aggregation propensity was determined by photon correlation spectroscopy (Zetasizer Nano series, Malvern Instruments Ltd., Worcestershire, UK). Robed-FAM-siRNA were dissolved in ddH$_2$O or octanol and sonicated for 30 minutes. Measurements were made at 25° C. with a fixed angle of 173°. Measurements were performed using a red laser to avoid interference from the FAM-labeled siRNA. Sizes quoted here are the number means for the robed-siRNA hydrodynamic diameter.

Statistical Analysis

Data reported are mean±SD except where otherwise noted. Where appropriate, statistical significance was confirmed by one way-ANOVA and post-hoc test or the two-tailed, unpaired Student's t-test in Microsoft Excel. The level of significance was set at $p<0.05$.

Results siRNAs robed with cationic moieties were synthesized to form an ionic liquid using a simple, scalable two-step process consisting of cation/anion exchange followed by acid-base neutralization (Schemes 1-3).

Benzyl dimethyl alkyl ammoniums were used as the IL moieties as described previously (Nishimura et al., *Biomaterials*, 26:5558-5563 (2005)). Three different alkyl chain lengths were used: octyl (BDOA), tetradecyl (BDTA), and stearyl (BDSA) (Table 5). Further, several different siRNA sequences were used including two different glyceraldehyde-3-phosphate dehydrogenase (GAPDH) knockdown sequences (abbreviated as siRNA1 and siRNA2) as well as a matrix metalloproteinase-12 (MMP-12) knockdown sequence (abbreviated as siRNA3) and a non-silencing control siRNA sequence (abbreviated as siRNA4) (Table 5). Complexes were then lyophilized to remove all residual water. 1:1 ion pairing and final compositions were confirmed using elemental analysis (Table 1). Specifically, percent weights of carbon, nitrogen, and hydrogen were not significantly different than expected values.

Robed-siRNAs were characterized by octanol/water partitioning ($P_{o/w}$) (Table 2). As expected all robed-siRNAs partition well into octanol. While naked siRNA1 was highly hydrophilic (Log $P_{o/w}$=−3.76±0.13), robed-siRNA1s were hydrophobic with Log $P_{o/w}$ ranging from 1.43±0.04 for BDOA-siRNA1 to 3.79±0.38 for BDTA-siRNA1. Similar results were observed regardless of the siRNA sequence used (Table 2). In addition, all robed-siRNAs were more hydrophobic than their corresponding benzyl dimethyl alkyl ammonium salt. For example, BDOA chloride is only slightly hydrophobic with Log $P_{o/w}$=0.85 (predicted value). In contrast, BDOA-siRNA1 was ~4-fold more hydrophobic.

TABLE 1

Synthesis of siRNA robed with IL moieties as verified using elemental analysis.

| Sample | % wt Carbon | | % wt Hydrogen | | % wt Nitrogen | | Carbon/ Nitrogen | |
|---|---|---|---|---|---|---|---|---|
| | Expected | Measured | Expected | Measured | Expected | Measured | Expected | Measured |
| siRNA1 | 33.8 | 32.0 (0.04) | 3.4 | 3.3 (0.07) | 14.4 | 14.4 (0.15) | 2.3 | 2.2 (0.02) |
| BDOA-siRNA1 | 56.0 | 55.8 (0.06) | 7.3 | 7.7 (0.10) | 11.2 | 11.4 (0.11) | 5.0 | 4.9 (0.05) |
| BDTA-siRNA1 | 68.4 | 69.0 (0.77) | 9.4 | 9.5 (0.11) | 11.2 | 11.3 (0.22) | 6.1 | 6.1 (0.18) |
| BDSA-siRNA1 | 76.7 | 76.1 (0.46) | 10.8 | 10.8 (0.04) | 11.2 | 11.3 (0.06) | 6.8 | 6.8 (0.03) |

Table 1 shows % wt of Carbon, Hydrogen, and Nitrogen and Carbon/Nitrogen ratio for FAM-siRNA1 and -siRNA1 robed with IL moieties. Standard deviation for n=3 is given in parentheses. Expected and measured values are shown and measured values compare well with expected values which strongly suggests incorporation of IL moieties.

TABLE 2 siRNA robed with IL moieties are significantly more hydrophobic than native siRNA and native IL moiety.

| | Log $P_{o/w}$ | | |
|---|---|---|---|
| | Chloride | siRNA1 | siRNA2 |
| Sodium | | −3.76 (0.13) | −3.80 (0.21) |
| BDOA | 0.85[1] | 1.43 (0.04) | 1.88 (0.16) |
| BDTA | 1.81[2] | 3.79 (0.38) | 4.27 (0.78) |
| BDSA | 3.23[3] | 2.31 (0.04) | 2.75 (0.33) |

Table 2 shows Log $P_{o/w}$ for FAM-siRNA1 and -siRNA2. Standard deviation for n=3 is given in parentheses. [1]Predicted value; [2]Hansch et al., Exploring QSAR—Hydrophobic, Electronic, and Steric Constants. Washington, D.C.: *American Chemical Society*, p. 182 (1995); [3]Hansch et al., *American Chemical Society*., p. 188 (1995).

The size and aggregation propensity of robed-siRNAs in octanol and water were determined using dynamic light scattering (DLS). In contrast to polyplexes which do not readily penetrate skin, siRNA robed with IL moieties at the molecular scale were produced that readily cross the skin barrier and reach skin cells. Since siRNA sequence does not appear to affect partitioning, only siRNA1 was studied here. Importantly, DLS measurement suggests robed-siRNA1 form individual complexes and do not aggregate in octanol (representative of the SC) (Table 3). Hydrophilic naked siRNA1 was not soluble in octanol and thus DLS was not performed. In water, however, the hydrodynamic diameter of naked siRNA1 was 1.06±0.32 nm. All robed-siRNAs were soluble in octanol. Hydrodynamic diameters of robed-siRNA1 in octanol were larger than for naked siRNA1 in water and increased with increasing alkyl chain length of the IL moieties. Aggregation was observed in water for BDTA and BDSA-siRNA1. Specifically, BDTA- and BDSA-siRNA1 possessed hydrodynamic diameters in water of 182.0±92.4 and 846.4±176.1 nm, respectively. In contrast, BDOA-siRNA1 was not observed to aggregate in water (hydrodynamic diameter=1.63±0.16 nm). As a control, the size of a siRNA polyplex (Lipofectamine® RNAiMax, Life Technologies, Grand Island, N.Y.) was also determined. Similar to naked siRNA1, RNAiMax-siRNA1 was insoluble in octanol thus DLS was not performed. In water, the hydrodynamic radius was 88.3±1.2 nm. Taken together the data show that robed-siRNAs do not aggregate in octanol and therefore may move through the hydrophobic SC as single complexes as opposed to polyplexes.

TABLE 3

DLS measurements of siRNA robed with IL moieties shows formation of individual complexes without aggregation in octanol (representative of the SC), while in water aggregation is dependent on alkyl chain length of the IL moiety.

| | Effective diameter (nm) in octanol | Effective diameter (nm) in water |
|---|---|---|
| siRNA1 | Insoluble | 1.06 (0.32) |
| BDOA-siRNA1 | 2.03 (0.33) | 1.63 (0.16) |
| BDTA-siRNA1 | 2.68 (0.52) | 182.0 (92.4) |
| BDSA-siRNA1 | 4.44 (1.29) | 846.4 (176.1) |
| RNAiMax-siRNA1 | Insoluble | 88.3 (1.2) |

Table shows effective complex diameters (nm) for robed-FAM-siRNA. Standard deviation for n=3 is given in parenthesis.

Example 2. Robed-siRNA is Efficiently Transported Through the Skin

Materials and Methods

Measurement of Skin Transport

Full thickness pig skin (Lampire Biological Laboratories, Pipersville, Pa.) was used in this study. All skin samples were stored at −80° C. Skin was defrosted and hair were trimmed immediately prior to use. Skin pieces were cleaned with PBS (pH 7.4) and skin conductivity was measured to ensure that the samples were intact. Skin penetration was assessed in Franz diffusion cells (FDCs) as described previously (Chen et al., *Journal of Controlled Release,* 179:33-41 (2014); Karande et al., *Nature Biotechnology,* 22:192-197 (2004)). Briefly, the receptor compartment was filled with PBS at pH 7.4. Each test formulation was assessed in triplicate. Skin was mounted with the SC facing up and the donor compartment left dry and open to atmosphere for 30 minutes before applying the test formulation. Caution was taken to remove all air bubbles between the underside of the skin (dermis) and the receptor solution. 150 μL of 50 μM FAM-siRNA or robed-FAM-siRNA was applied to skin surface. FDCs were incubated for 24 hours at 37° C. with moderate stirring. After 24 hours the formulations were removed from the skin by washing five times with PBS (pH 7.4). The SC was isolated from the epidermis by stripping with an adhesive tape (Scotch® Transparent Tape, 3M Corporate, St. Paul, Minn.). Ten tape strips were performed consecutively. The stripped tapes were collected in glass vials as follows: SC 1=1st strip and SC 2-10=2nd-10th strips. 10 strips were assumed to remove the entirety of the SC. After tape-stripping, the epidermis was isolated from the dermis with a surgical sterile scalpel. The epidermis and dermis were cut into small pieces and transferred into separate glass vials. Finally, 3 mL volume from the acceptor solution was transferred to glass vial. For extraction of fluorescent siRNA, 3 mL of methanol and PBS pH 7.4 (1:1, v/v) mixture was added to each vial and shaken overnight at room temperature. Afterwards the solutions were centrifuged for 10 minutes to pellet skin tissue. Supernatants were withdrawn, diluted if necessary, and concentrations of fluorescent probes were determined by fluorescence spectroscopy as described above.

Visualization of Skin Transport

To visualize transport of FAM-siRNA and robed-FAM-siRNA into skin, formulations were applied to skin in FDCs as described above. After incubation for 24 hours, thin sections (20 μm) corresponding to the application area were prepared using a Leica Cryostat CM1850 (Leica, Buffalo Grove, Ill.). Sections were imaged using an Olympus Fluoview 1000 Spectral confocal microscope (Olympus, Center Valley, Pa.). All instrument settings were kept constant between samples for comparison between experimental conditions.

Results

Figure 2A:
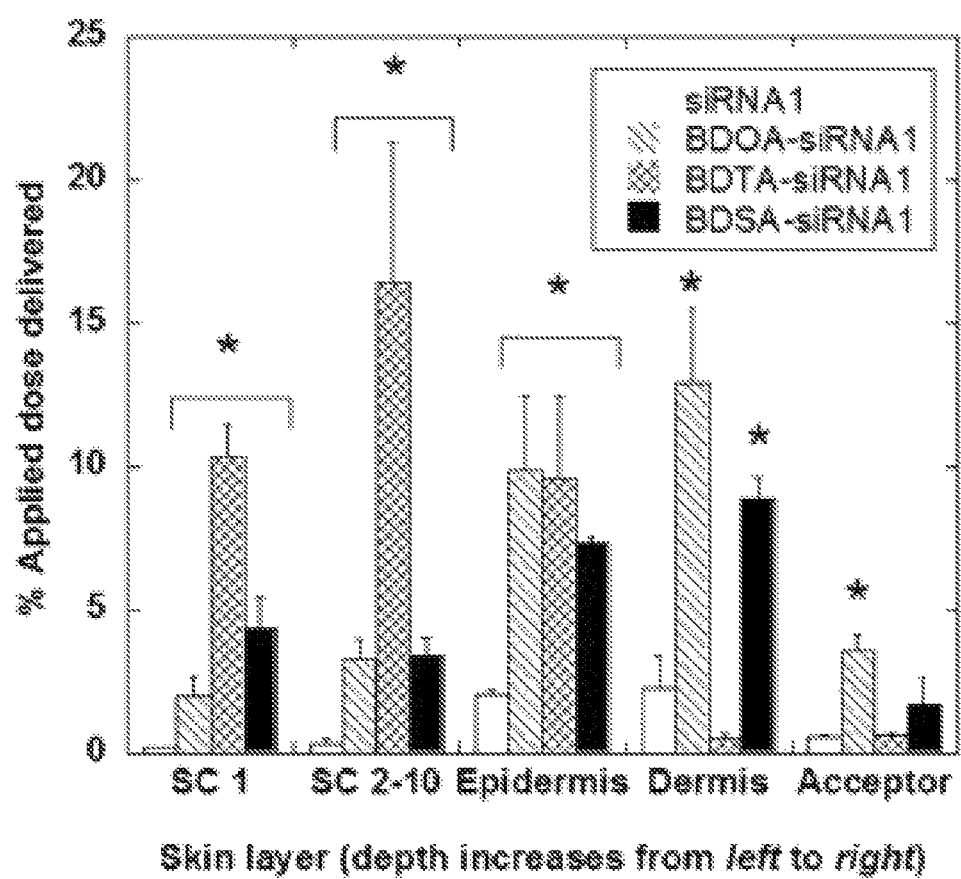
FIGS. 2A and 2B are bar graphs showing the percentage of the applied dose of free siRNA, or robed-siRNA delivered to different skin layers of porcine skin.
Figure 2B:
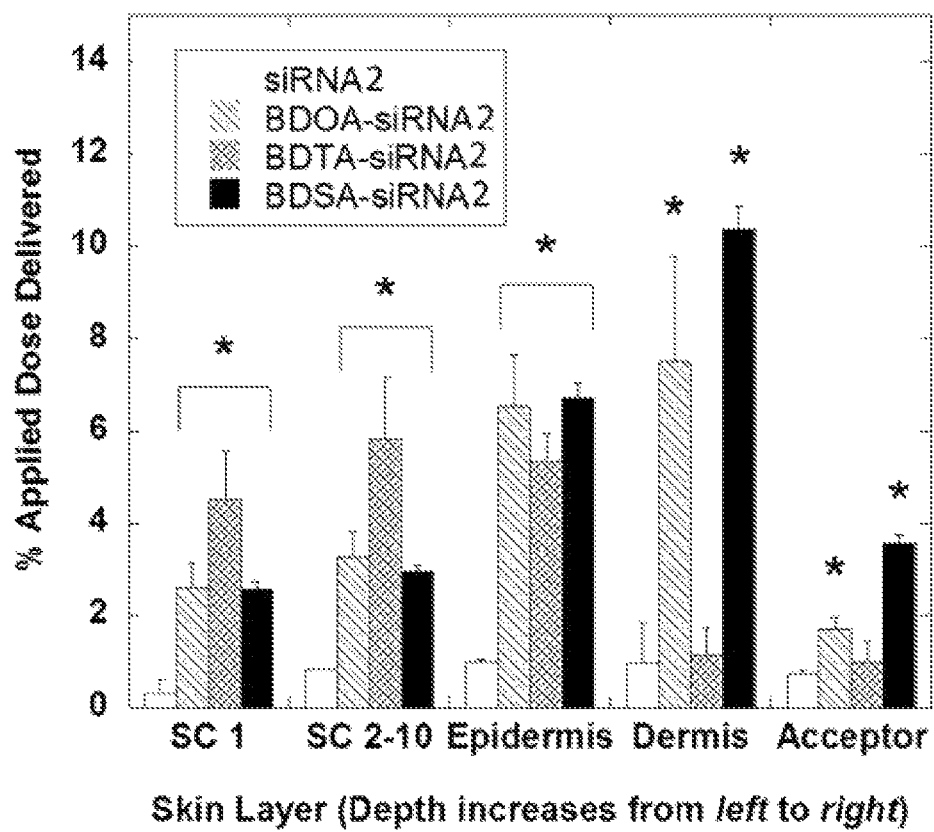

Skin penetration was assessed using Franz diffusion cells (FDCs) as described previously (Chen et al., *Journal of Controlled Release*, 179:33-41 (2014); Karande et al., *Nature Biotechnology*, 22:192-197 (2004)). Importantly, skin transport of siRNA1 was significantly enhanced by robing with IL moieties (FIGS. 2A and 2B). Percent (%) applied dose delivered into the viable epidermis was 9.85±2.64, 9.60±2.85, and 7.33±0.24 for BDOA-, BDTA-, and BDSA-siRNA1 compared to only 2.06±0.15 for naked siRNA1. Similarly, % applied dose delivered into the deeper skin tissue layer of the dermis was 12.94±2.56 and 8.89±0.77 for BDOA- and BDSA-siRNA1 compared to only 2.26±1.16 for naked siRNA1. Interestingly, % applied dose delivered into the dermis was actually retarded (0.49±0.18) when siRNA1 was robed with BDTA. Similar results were observed regardless of siRNA sequence used (FIG. 2B).

Delivery enhancement of robed-FAM-siRNA into skin was confirmed with confocal microscopy. Significantly higher skin transport of siRNA was observed when robing with IL moieties compared to unrobed siRNA Example 3. Robed-siRNA is Not Toxic to Cells Materials and Methods
Cell Culture All cell culture materials were acquired from Life Technologies (Grand Island, N.Y.). Human adult epidermal keratinocytes were cultured in EpiLife Medium supplemented with Human Keratinocyte Growth Supplement, 25 U/mL penicillin, 25 μg/mL streptomycin, and 50 μg/mL neomycin. Cultures were grown at 37° C. with 5% CO2.

Evaluation of Biocompatibility in Cell Culture

Cells were seeded in a 96-well microplate (Corning Inc., Corning, N.Y.) and were allowed to attach and proliferate. Once cells reached ~80% confluency, the media was removed and FAM-siRNA, robed-FAM-siRNA, or benzyl dimethyl alkyl ammonium chloride salts in media was added. Media alone was used as a control. Cells were incubated with test solution for 4 hours at 37° C. and 5% $CO_2$. After incubation, test solutions were removed, cells were washed with HBSS, and fresh media was added to each well. Cells were allowed to proliferate overnight before being assessed for viability using the MTT Cell Proliferation Assay (ATCC, Manassas, Va.). Viability was determined according to the manufacturer's recommended protocol using a SAFIRE, XFLUOR4, V4.50 microplate reader (Tecan Group Ltd, Morrisville, N.Y.).

Results

The ability of robed-siRNA to cross cell membranes was assessed in vitro by confocal laser scanning microscopy (CLSM). Human adult epidermal keratinocytes (HEKa cells) are the primary cell type in the viable epidermis and thus were used for all in vitro studies. HEKa cells were incubated with 100 nM robed-siRNA1 for 4 hours. Cells were then washed, nuclei stained with Hoechst 33342, and imaged to visualize siRNA1 internalization. Internalization of robed-siRNA1 was compared to internalization of naked siRNA1. Importantly, compared to naked siRNA1, cell internalization was enhanced by robing with IL moieties. On the other hand, the extent of cell internalization does appear to depend on the IL moiety used. For example, BDTA showed the most internalization enhancement while BDOA showed the least enhancement.

Figure 3A:
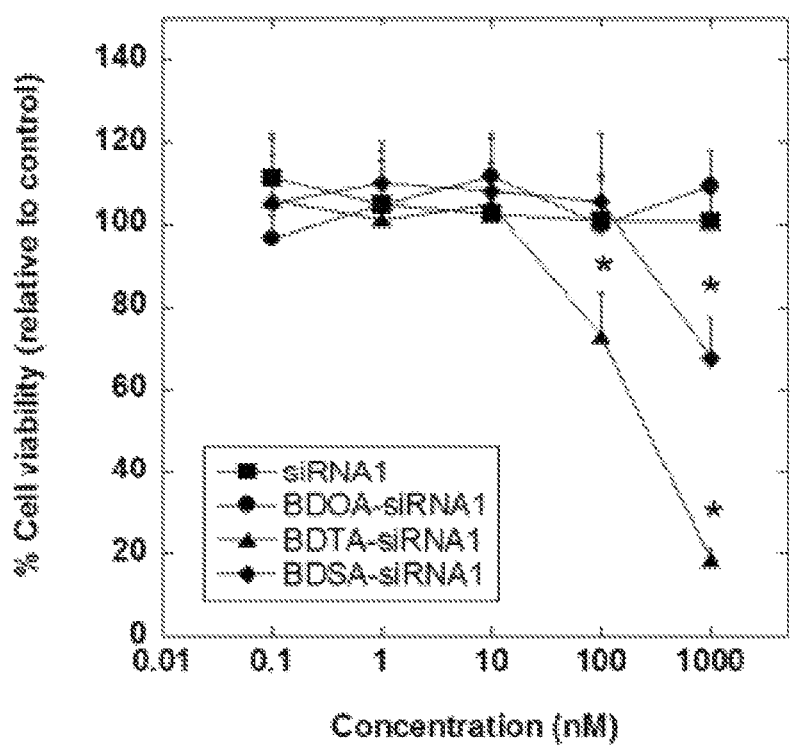
Figure 3B:
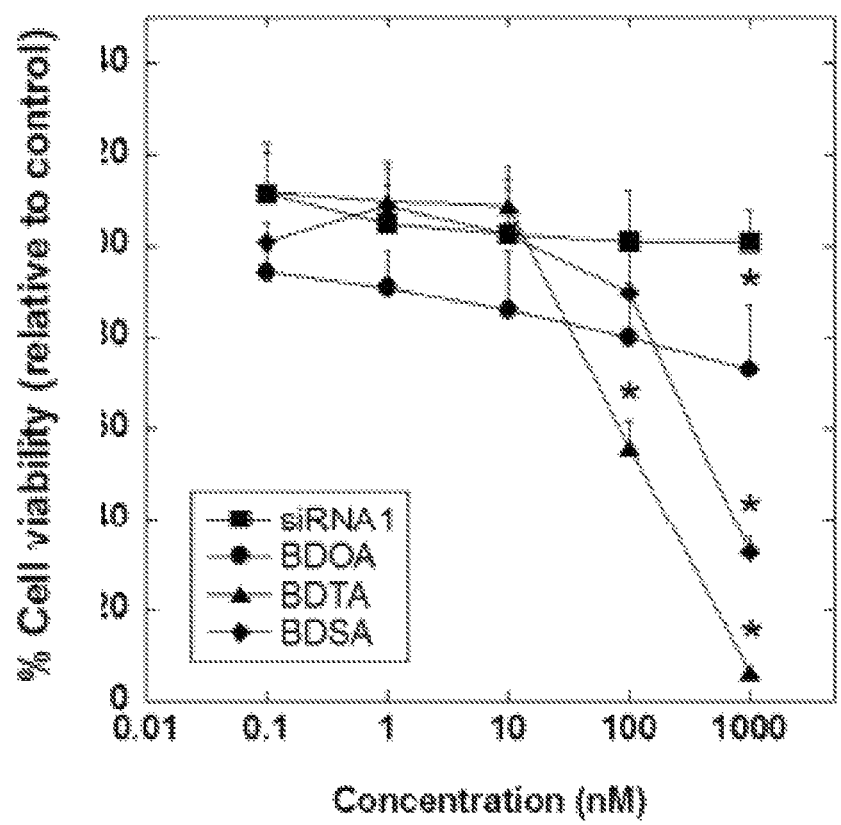
Figure 3C:
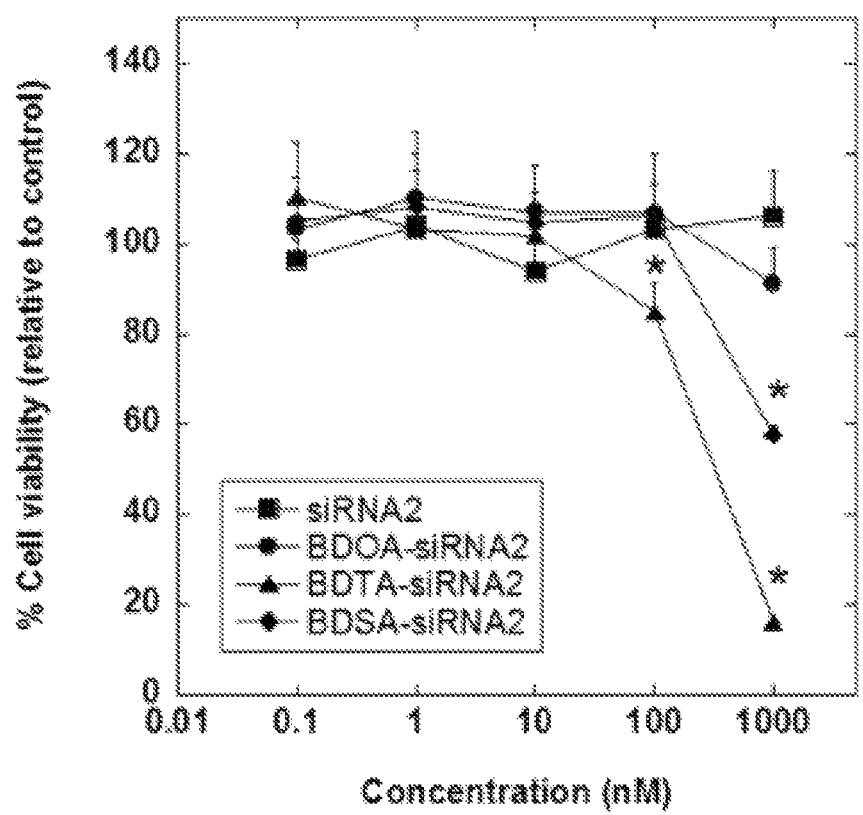

Biocompatibility of robed-siRNAs was assessed in vitro against HEKa cells using the MTT assay (ATCC, Manassas, Va.). Importantly, robed-siRNA1 shows negligible cytotoxicity to HEKa cells up 100 nM (FIG. 3A). Above 100 nM, however, cytotoxicity was observed for BDTA-siRNA1 and BDSA-siRNA1. Specifically, following incubation with 1000 nM BDTA- or BDSA-siRNA1% cell viability was 18.48±2.66 and 67.60±9.92 compared to HEKa cells incubated with culture media alone. In contrast, no significant cytotoxicity was observed following incubation with 1000 nM BDOA-siRNA1. Naked siRNA1 was non-toxic for all concentrations studied (FIGS. 3A-3C). In addition, BDOA, BDTA, and BDSA appear to be more toxic as free salts than when deliver as robed with siRNAs (FIG. 3B). This observation was most apparent at higher concentrations; however, the differences were not statistically significant (p>0.05). Again, similar results were observed regardless of the siRNA sequence used (FIG. 3C).

Example 4. Robed-siRNA is Successfully Internalized in Skin Cells

Materials and Methods

Cells were seeded on poly-D-lysine-coated glass bottom culture dishes (MatTek Corporation, Ashland, Mass.) and were allowed to attach and proliferate. Once cells reached ~80% confluency, the media was removed and FAM-siRNA or robed-FAM-siRNA in media was added. Cells were incubated with test formulations for 4 hours under standard culture conditions. After incubation with test solutions, cells were stained with 5 μg/mL Hoechst 33342 (Life Technologies, Grand Island, N.Y.) for 5 min at room temperature and then washed 3 times for 5 min each with Hank's Balanced Salt Solution (HBSS, Lonza Group Ltd., Basel, Switzerland). Cells were imaged using an Olympus Fluoview 1000 Spectral confocal microscope (Olympus, Center Valley, Pa.). All instrument settings were kept constant for any comparisons between experimental conditions and a 30× silicon immersion objective was used to capture the entire thickness of the cell.

Results

Figure 4:
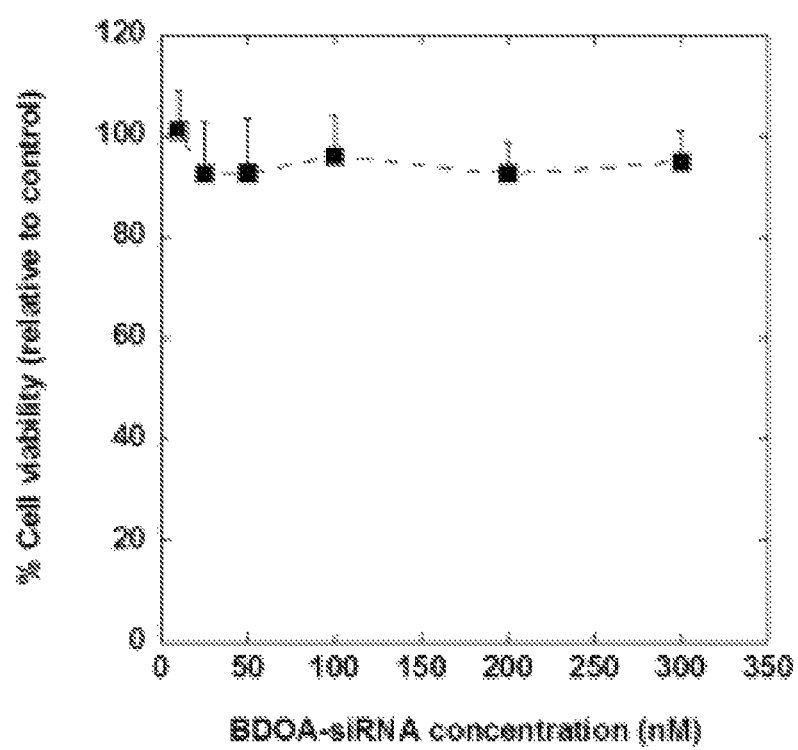

BDOA-siRNA demonstrated excellent transport into deep viable skin layers (epidermis and dermis), the ability to improve cell internalization compared to naked siRNA, and superior biocompatibility compared to BDTA- and BDSA-siRNA (FIGS. 2A-3C). Since siRNA in cell culture typically requires extended incubation times to elicit a response, BDOA-siRNA cell internalization and biocompatibility was also confirmed following 72 hour incubation. As expected, cell internalization in HEKa cells was significantly enhanced following 72 hour exposure to BDOA-siRNA1 compared to naked siRNA1. Further, negligible cytotoxicity was observed up to 300 nM BDOA-siRNA relative to cells incubated with media alone (FIG. 4).

As an additional control, cell internalization of BDOA-siRNA1 was compared to Lipofectamine RNAiMax-siRNA1. In contrast to RNAiMax-siRNA1, BDOA-siRNA1 shows significantly less cell internalization. Interestingly, however, the internalization pattern of BDOA-siRNA1 was strikingly different. Specifically, BDOA-siRNA1 demonstrated diffuse fluorescence indicative of cytoplasmic localization. In contrast, RNAiMax-siRNA1 demonstrated punctate fluorescence indicative of endosomal sequestration.

Example 5. Robed-siRNA Successfully Silences Gene Expression in Cells

Materials and Methods

Cells were seeded in a 96-well microplate (Corning Inc., Corning, N.Y.) and were allowed to attach and proliferate. Once cells reached ~80% confluency, media was removed and FAM-siRNA or robed-FAM-siRNA in media was added. Media alone was used as a control. Cells were incubated with test solution for 72 hours at 37° C. and 5% $CO_2$. After incubation, total protein and GAPDH expression were quantified. Total protein was assessed with the Bicinchoninic Acid Protein Assay Kit (Thermo Scientific, Rockford, Ill.) and GAPDH levels were measured using the KDalert GAPDH Assay Kit (Life Technologies, Grand Island, N.Y.) according to the manufacturer's recommended protocol and using a SAFIRE, XFLUOR4, V4.50 microplate reader (Tecan Group Ltd, Morrisville, N.Y.).

Results

Figure 5:
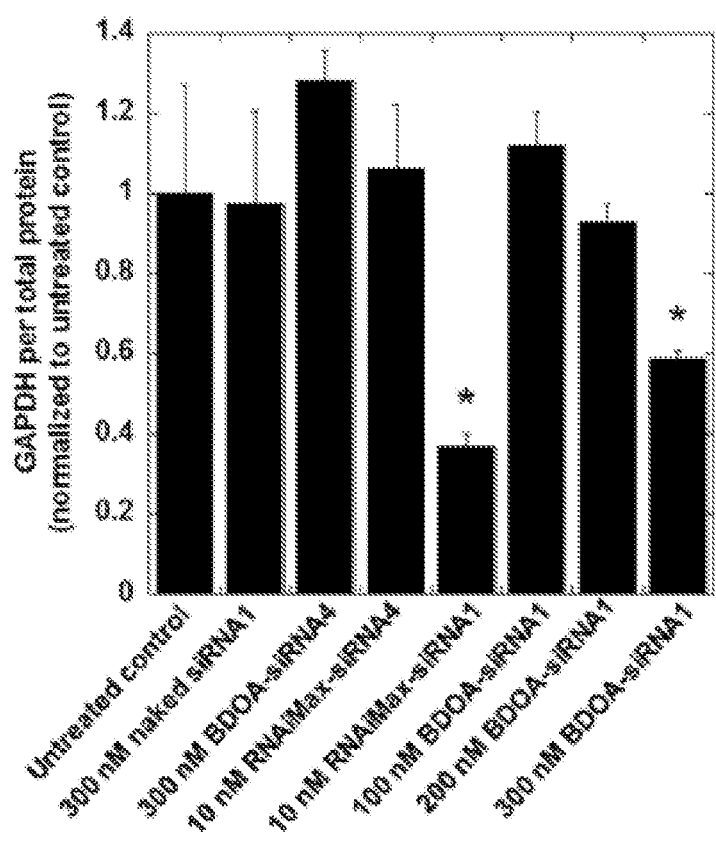

The ability of BDOA-siRNA to elicit a therapeutic response was first confirmed in vitro. GAPDH was used as a model knockdown target. BDOA-siRNA1 was incubated with HEKa cells at various concentrations and GAPDH knockdown was assessed as described previously (Chen et al., *Journal of Controlled Release*, 179:33-41 (2014)). As controls, naked siRNA1 and BDOA-siRNA4 (non-silencing control siRNA) were also studied. As an additional control RNAiMax-siRNA1 and RNAiMax-siRNA4 were also used at the manufacturer's recommended concentration (10 nM). As expected, naked siRNA1 as well as non-silencing siRNA4 formulations did not reduce GAPDH expression in HEKa cells after 72 hour incubation (FIG. 5). In addition, 100 nM and 200 nM BDOA-siRNA1 showed no significant difference in GAPDH expression compared to the untreated control. Incubation with 300 nM BDOA-siRNA1, however, did result in significant GAPDH knockdown (58.7±2.0% GAPDH expression compared to the untreated control) (FIG. 5). Similarly, incubation with 10 nM RNAiMax-siRNA1 resulted in significant GAPDH knockdown (36.9±3.2% GAPDH expression compared to the untreated control).

Example 6. Robed-siRNA Disease Treatment and Biocompatibility in MatTek Epiderm™ Tissue Samples Materials and Methods MatTek Epiderm™ human skin equivalent tissues were used as described previously (Afaq et al., *Exp Dermatol*, 18:553-561 (2009)) to evaluate treatment of premature wrinkle formation using robed-siRNA. Briefly, Epiderm™ tissues were allowed to acclimate at 37° C. and 5% $CO_2$ for 24 hours with 2.5 mL media in 6-well culture plates (Corning Inc., Corning, N.Y.). After 24 hours incubation, media was replaced and 100 µL of dd$H_2O$ (control) or 50 µM native elastase siRNA (siRNA3), 50 µM BDOA-control non-silencing siRNA (siRNA4), 25 µM BDOA-siRNA3, or 50 µM BDOA-siRNA3 was applied to the apical side of the skin tissues. After 24 hours incubation, test formulations were removed and the skin was exposed to 200 mJ/cm2 UVB irradiation using a 6-watt UV lamp with 302 nm wavelength and white light tubes (Cole Parmer, Vernon, Ill.). Irradiation was measured with a Solarmeter model 6.2 UV meter (Solar Light Company Inc., Glenside, Pa.). Following exposure freshly prepared formulations were reapplied to the skin tissues and incubated for an additional 96 hours. At the conclusion of the experiment, 2 mL of media was collected and analyzed for elastin and elastase content using a Human Elastin ELISA kit and Human MMP-12 ELISA kit (Biomatik USA LLC., Wilmington, Del.), respectively, following the manufacturer's recommended protocol. Biocompatibility of the test formulations was confirmed using the MTT assay following MatTek's recommended protocol.

Results

Figure 6:
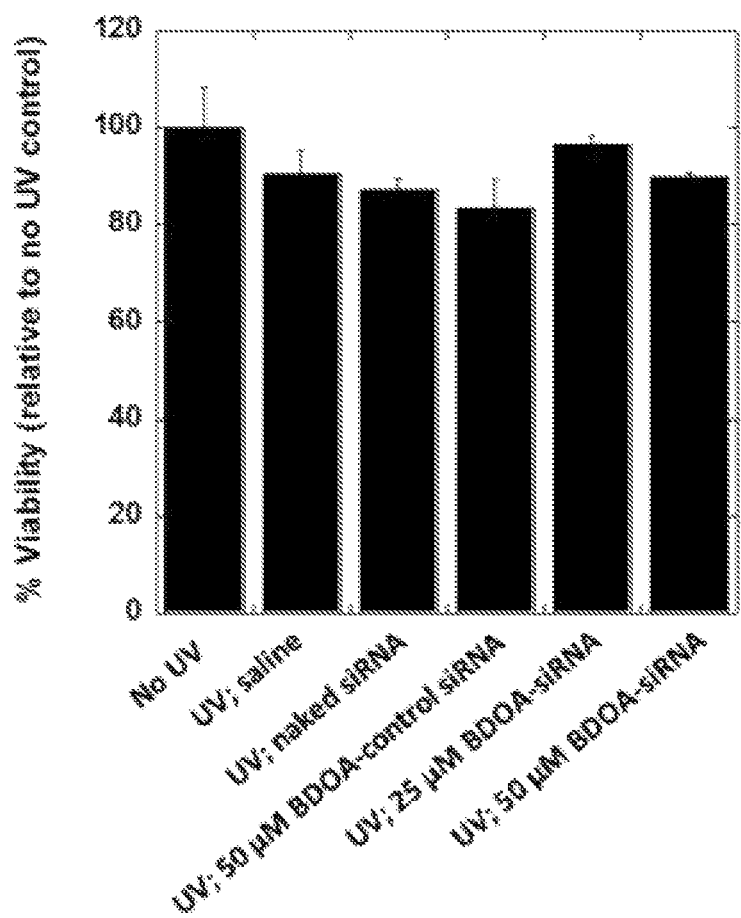
Figure 7A:
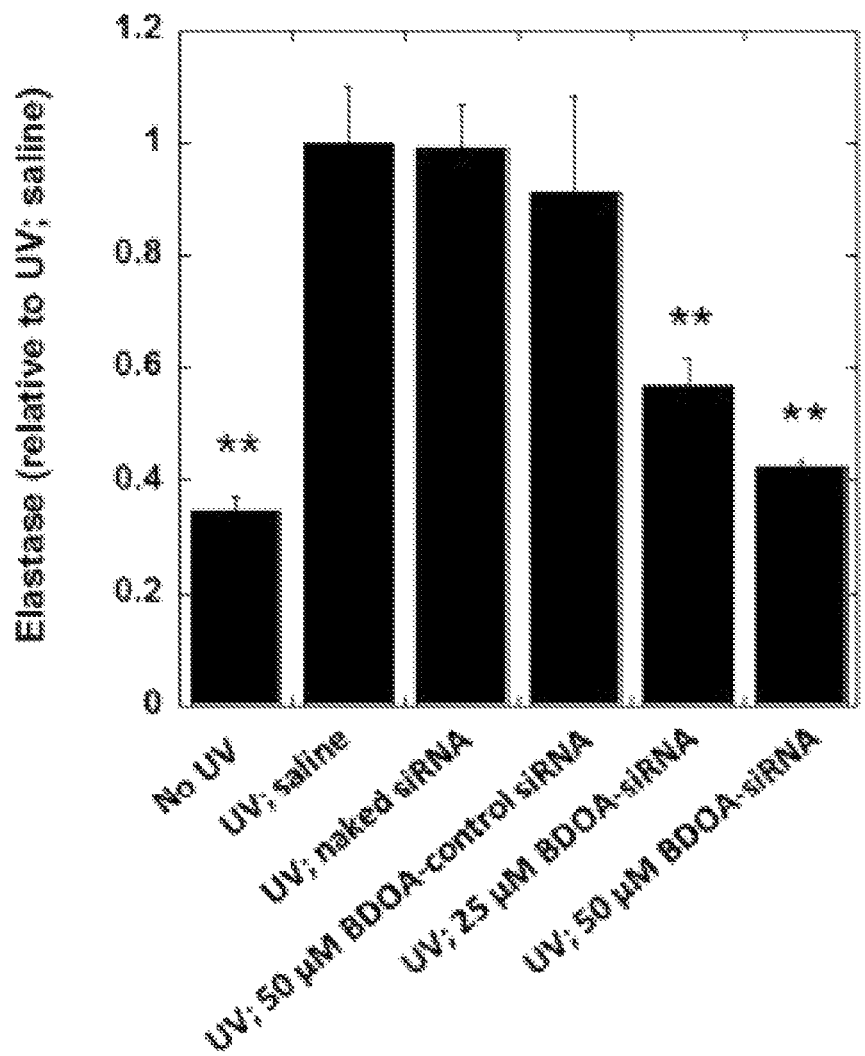
Figure 7B:
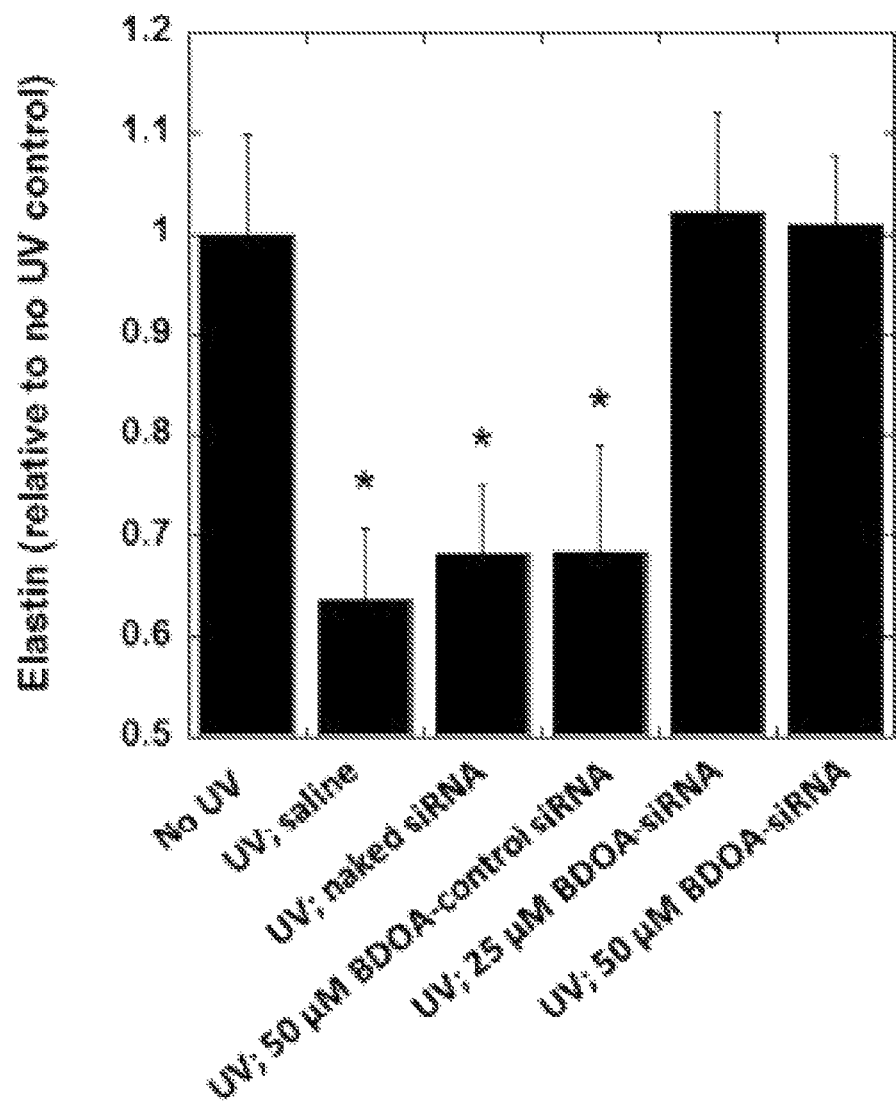

The clinical potential of BDOA-siRNA was assessed against a skin aging model in human skin equivalent tissues (Afaq et al., *Exp Dermatol*, 18:553-561 (2009)). Elastase upregulation has been proposed as an important factor for ultraviolet irradiation induced wrinkle formation (Tsuji et al., *Photochemistry and Photobiology*, 74:283-290 (2001)). Therefore, knockdown of elastase with topically applied RNAi is a proposed option for the treatment and prevention of skin wrinkling. Following UVB irradiation and application of BDOA-siRNAs there was no observed decrease in tissue viability (FIG. 6). This result confirms 1) irradiation of a suberythemal dose and 2) biocompatibility of BDOA-siRNA. Moreover, UVB irradiation resulted in significant upregulation of elastase (FIG. 7A) and significant reduction in elastin (FIG. 7B) compared to tissues not exposed to UVB irradiation confirming the validity of the disease model. Topical application of naked siRNA3 or BDOA-siRNA4 was unable to protect against elastase upregulation and consequent elastin degradation. In contrast, application of BDOA-siRNA3 at both 50 µM and 25 µM were able to maintain the non-altered state of the skin following UVB irradiation thus confirming the clinical potential of robed-siRNAs (FIGS. 7A and 7B).

Example 7. Cation Paired Hyaluronic Acid (HA) is an Efficient skin Penetration Agent Materials and Methods Cation paired HA was prepared according to methods described in Example 1.

Results

Different species of cation paired HA and their octanol-water partition coefficients are show in Table 4. The pairing of hydrophobic cations with hyaluronic acid dramatically enhances their octanol-water partition coefficient. This enhancement in octanol-water partition coefficient is expected to increase their skin penetration. Pairing of hyaluronic acid with hydrophobic cations led to up to 1,000,000-fold improvement in their octanol-water partition coefficient, similar to those seen for siRNA. Such dramatic enhancement in partition coefficient is expected to increase their skin penetration.

TABLE 4

Exemplary cations paired with HA and their octanol-water partitioning coefficients.

| Cations paired with HA | LogP$_{o/w}$ |
|---|---|
| Na+<br>Sodium | −3.69 |
| 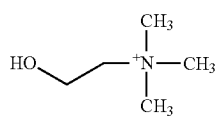<br>Hydroxyethyltrimethyl ammonium | −3.32 |

TABLE 4-continued

Exemplary cations paired with HA and their octanol-water partitioning coefficients.

| Cations paired with HA | LogP$_{o/w}$ |
|---|---|
| CH$_3$(CH$_2$)$_{12}$CH$_2$—N$^+$(CH$_3$)$_3$ Br$^-$  Tetradecyltrimethyl ammonium | 2.14 |
| Benzyl—N$^+$(CH$_3$)$_2$—CH$_2$(CH$_2$)$_{12}$CH$_3$  Benzyldimethytetradecyl ammonium | 2.53 |
| Benzyl—N$^+$(CH$_3$)$_2$—CH$_2$(CH$_2$)$_{16}$CH$_3$  Benzyl dimethyl stearyl ammonium (BDSA) | 2.40 |

Example 8. Dermal Delivery of Bovine Serum Albumin and Ovalbumin in the Presence of Choline-Geranic Acid IL Materials and Methods Choline and geranic acid deep eutectic liquid was prepared as described in WO 2015/066647, and fluorescently-labeled albumin (bovine serum albumin or ovalbumin) was added to it. Albumin-loaded choline-geranic acid formulation was placed on porcine skin for 24 hours and skin was sectioned to assess the penetration of albumin Control experiments were performed using PBS.

Results

Significant and deep penetration of albumin was seen when albumin was delivered from choline and geranic acid. The benefits of choline and geranic acid formulation are expected to extend to other proteins including insulin, antibodies, and therapeutic peptides. The benefits of choline and geranic acid are also expected to extend to other ionic liquids.

BDOA-siRNA exhibited the most enhancement into the deep viable tissue layers of the skin (epidermis and dermis) (FIGS. 2A and 2B). In addition, although cell internalization was less efficient compared to BDTA- and BDSA-siRNA, BDOA-siRNA shows negligible cytotoxicity to skin cells at significantly higher concentrations (FIGS. 3A-3C).

The ability of BDOA-siRNA to prevent wrinkle formation was assessed against a skin aging model in human skin equivalent tissues as described previously (Afaq et al., *Exp Dermatol*, 18:553-561 (2009)). BDOA robed-antielastase siRNA was applied on the apical surface of human skin equivalent tissues. As controls, saline, naked anti-elastase siRNA, and BDOA robed-non-silencing control siRNA were also tested. UVB irradiation induced significant elastase upregulation and elastin degradation in control tissues (FIGS. 7A and 7B). In contrast, tissues treated with 25 μM or 50 μM BDOA robed-antielastase siRNA showed identical elastase and elastin content as unexposed, healthy tissues (i.e. no UVB treatment).

Efficacy and safety of BDOA-siRNA is related to its physicochemical properties. The extent of transport correlates well with hydrophobicity of robed-siRNAs. Naked siRNA is hydrophilic and transport through the SC is minimal (FIGS. 2A and 2B). In contrast, the hydrophobic robed-siRNAs were able to penetrate the SC in significant quantities. BDTA was the most hydrophobic and transport into the SC was highest. However, due to high fusogenicity between BDTA and SC lipids, BDTA-siRNA was retained in superficial layers of the skin and did not penetrate into deep tissue layers. Thus, a balance must be sought to allow enhanced partitioning into the SC from the donor solution as well as out of the SC into viable tissue layers of the skin. Cell internalization of robed-siRNAs also correlates well with hydrophobicity. Log P$_{o/w}$ of BDTA-siRNA was highest among robed-siRNAs, and BDTA-siRNA1 possessed the highest degree of cell internalization. In contrast, Log P$_{o/w}$ of BDOA-siRNA was lowest among robed-siRNAs, and BDOA-siRNA1 possessed the lowest degree of cell internalization albeit still significantly higher than was observed for naked siRNA1.

The relationships between hydrophobicity and transport properties of robed-siRNAs presents an opportunity for tuning their efficacy through facile manipulation of the IL moiety counter species. Hydrophobicity appears tunable to an extent by varying the alkyl chain length of the counter species. Robing with BDOA resulted in the lowest Log P$_{o/w}$ while BDTA and BDSA-siRNAs were significantly more hydrophobic. However, the relation between hydrophobicity and chain length was not linear. Specifically, BDTA (alkyl chain=14 carbons) was significantly more hydrophobic than BDSA (alkyl chain=18 carbons). This is in contrast to the Log P$_{o/w}$ of individual benzyl dimethyl alkyl ammonium species which increase linearly with chain length (FIG. 1, r$^2$=0.9497) according to predicted and experimentally determined values. Aggregation propensity and the size of aggregates also appear to depend on alkyl chain length (Table 3). Ideally, robed-siRNAs would transport as single, hydrophobic molecules as opposed to polyplexes to maximize transdermal and transcellular transport. Aggregation into polyplexes is expected to significantly hinder the kinetics of skin transport as well as the depth of delivery thus aggregation should be avoided through optimization of the IL moiety alkyl chain length. Exemplary cations, with sodium ion used as control, and anions are shown in Table 5.

TABLE 5

Exemplary cations and anions used in the studies.

| Cations | Anions |
|---|---|
| Na+  Sodium | GACGUAAACGGCCACA AGUUCUU SEQ ID NO: 5  UUCUGCAUUUGCCGGU GUUCAAG SEQ ID NO: 6  siRNA1 (GAPDH) |
| Benzyl—N$^+$(CH$_3$)$_2$—CH$_2$(CH$_2$)$_6$CH$_3$  Benzyl dimethyl octyl ammonium (BDOA) | GUGUGAACCACGAGAA AUAUUUU SEQ ID NO: 7  UUCACACUUGGUGCUC UUUAUAA SEQ ID NO: 8  siRNA2 (GAPDH) |

TABLE 5-continued

Exemplary cations and anions used in the studies.

| Cations | Anions |
|---|---|
| 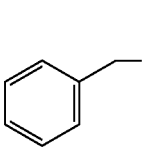<br>Benzyl dimethyl tetradecyl ammonium (BDTA) | UCACUUACAGGAUCUA GAAUU SEQ ID NO: 9<br>UUAGUGAAUGUCCUAG AUAUU SEQ ID NO: 10<br>siRNA3 (Elastase) |
| 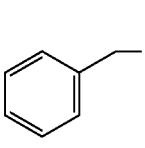<br>Benzyl dimethyl stearyl ammonium (BDSA) | UAAGGCUAUGAAGAGA UACUU SEQ ID NO: 11<br>UUAUUCCGAUACUUCU CUAUG SEQ ID NO: 12<br>siRNA4 (Control) |

Lipofectamine RNAiMax is a commercially available siRNA polyplex platform that has been optimized over many years to afford consistent, fast, and efficient delivery of siRNA into cells. RNAiMax-siRNA outperformed BDOA-siRNA at 30-fold lower concentrations (FIG. 5). Therefore, the data do not support the use of BDOA-siRNA for gene-silencing applications in cell culture in vitro. The difference could be related to the stability of robed-siRNAs in aqueous solution. RNAiMax-siRNA polyplexes are stable in high salt and buffered solutions while robed-siRNAs are held together simply by 1:1 ion pairing and thus are expected to dissolve in dilute aqueous conditions. Maximizing ion association between siRNA phosphate groups and the IL moiety may be one potential option to mitigate dissociation and subsequently maximize cell internalization and gene silencing at lower concentrations in solution. Ionic liquids are known to have varying degrees of ion association both neat as well as in solution depending on the choice of ion pairing (Zhang et al., *Journal of Physical and Chemical Reference Data*, 35:1475-1517 (2006)).

High concentrations of benzyl dimethyl alkyl ammonium robed-siRNA needed to minimize dissociation were also met with significant observed cytotoxicity. As with transport properties, cytotoxicity correlates well with hydrophobicity. This is not surprising given hydrophobicity is commonly used as an indicator for IL moiety cytotoxicity (Ranke et al., *Ecotoxicology and Environmental Safety*, 58:396-404 (2004); Ranke et al., *Ecotoxicology and Environmental Safety*, 67:430-438 (2007)) but may impose some limitations of robed-siRNA use as a balance may need to be struck between transport enhancement into skin and cells and biocompatibility. Interestingly, however, robed siRNAs do appear to be less toxic than equal concentrations of the IL moiety chloride salts (FIGS. 3A-3C). This suggests ion pairing may reduce cytotoxicity of the individual components somewhat which is in agreement with previous studies of ionic liquid toxicity (Aoyagi et al., *TECHNOLOGY*, 03:214-238 (2015); Zakrewsky et al., *Proceedings of the National Academy of Sciences*, 111:13313-13318 (2014)).

On the other hand, no toxicity effects were observed in human skin equivalent tissues. Therefore, biocompatibility may only be an issue for extending this strategy for knockdown in cell culture or following systemic administration in vivo. Cell internalization enhancement relative to naked siRNA and avoidance or release from endosomal compartments in combination with excellent dermal delivery highly supports the use of BDOA-siRNA for gene silencing applications in skin. Indeed, the skin presents a unique environment where robed siRNAs can penetrate through the hydrophobic SC as single complexes and then interact immediately with diseased cells in the viable epidermis, thus limiting the extent of dissociation and enhancing cell internalization and gene silencing. This is consistent with the observations after application of BDOA-siRNA on human skin equivalent tissues (FIGS. 6, 7A and 7B). In addition, robed-siRNA properties and behavior are independent of siRNA sequence. This opens up the possibilities of using robed-siRNAs for the treatment of myriad other skin diseases for which known protein knockdown targets exist such as psoriasis, atopic dermatitis, skin cancer, melasma, pachyonychia congenita, and many others (Zakrewsky et al., *Journal of Controlled Release*, 218:445-456 (2015)). Further, this opens up the possibility for more effective treatments through the use robed-siRNA cocktails that knockdown several protein targets simultaneously.

Therefore, knockdown of elastase with topically applied RNAi may be a viable option for the treatment and prevention of skin wrinkling, as well as provide patients with a safe alternative to current options. Topically applied RNAi must transport through the skin and into cells to elicit a therapeutic response. In addition, the therapy must be biocompatible.

We claim:

1. A composition for transdermal delivery of a macromolecule comprising a complex comprising
   an anion of the macromolecule, and
   a cation;
   wherein the complex is charge neutral, and wherein the composition is in a form suitable for topical application to the skin.

2. The composition of claim 1, wherein the macromolecule is selected from the group consisting of nucleic acids, peptides, proteins, and polysaccharides.

3. The composition of claim 1, wherein the macromolecule is an RNA interference molecule selected from the group consisting of microRNA (miRNA), short hairpin RNA (shRNA), and small interfering RNA (siRNA).

4. The composition of claim 1, wherein the macromolecule is a double stranded siRNA, wherein each strand has a length ranging from 20 to 25 nucleotides.

5. The composition of claim 1, wherein the macromolecule is a polysaccharide.

6. The composition of claim 1, wherein the cation comprises an alkyl chain with a length ranging from three carbon atoms to twenty carbon atoms.

7. The composition of claim 1, wherein the cation has the structure of Formula II:

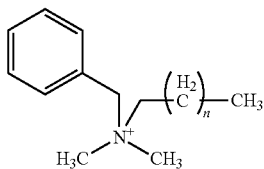

Formula II wherein n is an integer ranging from 3 to 19, inclusive.

8. The composition of claim 7, wherein the cation is not benzyldimethyldodecyl ammonium.

9. The composition of claim 7, wherein the cation is selected from the group consisting of benzyldimethyloctyl ammonium, benzyldimethyltetradecyl ammonium, and benzyldimethylstearyl ammonium.

10. The composition of claim 1, wherein the hydrophobicity of the complex, as determined by its octanol/water partition coefficient (Po/w), is increased by at least one log unit (Log Po/w) compared to the hydrophobicity of the anion of the macromolecule when it is complexed with a sodium cation.

11. The composition of claim 1, wherein the cation has the structure of Formula I,

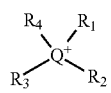

Formula I wherein Q is nitrogen (N) or phosphorus (P), wherein $R_1$, $R_2$, $R_3$, and $R_4$ are independently hydrogen, substituted alkyl, unsubstituted alkyl, substituted alkenyl, unsubstituted alkenyl, substituted alkynyl, unsubstituted alkynyl, substituted alkoxy, unsubstituted alkoxy, substituted amino, unsubstituted amino, substituted alkylamino, unsubstituted alkylamino, substituted alkylthio, or unsubstituted alkylthio, substituted aryl, unsubstituted aryl, substituted heteroaryl, unsubstituted heteroaryl, substituted $C_3$-$C_{30}$ cycloalkyl, unsubstituted $C_3$-$C_{30}$ cycloalkyl, substituted heterocyclyl, unsubstituted heterocyclyl, and any pair of $R_1$, $R_2$, $R_3$, and $R_4$ independently combine to form five- and/or six-membered rings, wherein the five- and/or six-membered rings formed from combining any pair of $R_1$, $R_2$, $R_3$, and $R_4$ optionally including an additional heteroatom.

12. The composition of claim 11, wherein the cation is not cetyltrimethyl ammonium, decyltrimethyl ammonium, benzyldimethyldodecyl ammonium, myristyltrimethyl ammonium, or dodecyl pyridinium.

13. The composition of claim 11, wherein at least one of $R_1$, $R_2$, $R_3$, and $R_4$ is independently a substituted alkyl, wherein the substituted alkyl is a substituted aralkyl or unsubstituted aralkyl.

14. The composition of claim 11, wherein at least one of $R_1$, $R_2$, $R_3$, and $R_4$ is independently a substituted alkyl, wherein the substituted alkyl is a substituted aralkyl or unsubstituted aralkyl, with the proviso that the cation is not benzyldimethyl dodecyl ammonium.

15. The composition of claim 11, wherein $R_1$ is independently a substituted alkyl, wherein the substituted alkyl is a substituted aralkyl or unsubstituted aralkyl, wherein $R_2$, $R_3$, and $R_4$ are independently substituted alkyl or unsubstituted alkyl, with the proviso that when $R_2$, $R_3$, and $R_4$ are substituted alkyls, the substituted alkyl is not a substituted aralkyl or unsubstituted aralkyl, and with the proviso that the cation is not benzyldimethyl dodecyl ammonium.

16. A method of treating one or more skin conditions in a subject in need thereof, the method comprising topically administering to the skin of the subject an effective amount of the composition of claim 1.

17. The method of claim 16, wherein prior to, subsequent to or simultaneous with the step of topically administering the composition, the skin is not subjected to additional treatments to increase the porosity of the skin, remove all or a portion of the stratum corneum, push the complex through the stratum corneum, or otherwise aid in transport of the composition or the complex through one or more layers of the skin.

* * * * *

SEQUENCE LISTING

<160> NUMBER OF SEQ ID NOS: 12

<210> SEQ ID NO 1
<211> LENGTH: 21
<212> TYPE: RNA
<213> ORGANISM: Artificial Sequence
<220> FEATURE:
<223> OTHER INFORMATION: FAM-GAPDH siRNA, shown 5' to 3'
<220> FEATURE:
<221> NAME/KEY: misc_feature
<222> LOCATION: (1)..(1)
<223> OTHER INFORMATION: 5' FAM modification

<400> SEQUENCE: 1
gacguaaacg gccacaaguu c                                              21

```
<210> SEQ ID NO 2
<211> LENGTH: 21
<212> TYPE: RNA
<213> ORGANISM: Artificial Sequence
<220> FEATURE:
<223> OTHER INFORMATION: FAM-GAPDH siRNA, shown 5' to 3'
<220> FEATURE:
<221> NAME/KEY: misc_feature
<222> LOCATION: (1)..(1)
<223> OTHER INFORMATION: 5' FAM modification

<400> SEQUENCE: 2
gugugaacca cgagaaauau u                                          21

<210> SEQ ID NO 3
<211> LENGTH: 21
<212> TYPE: RNA
<213> ORGANISM: Artificial Sequence
<220> FEATURE:
<223> OTHER INFORMATION: FAM-Elastase siRNA, shown 5' to 3'
<220> FEATURE:
<221> NAME/KEY: misc_feature
<222> LOCATION: (1)..(1)
<223> OTHER INFORMATION: 5' FAM modification

<400> SEQUENCE: 3
ucacuuacag gaucuauaau u                                          21

<210> SEQ ID NO 4
<211> LENGTH: 21
<212> TYPE: RNA
<213> ORGANISM: Artificial Sequence
<220> FEATURE:
<223> OTHER INFORMATION: FAM siRNA, shown 5' to 3'
<220> FEATURE:
<221> NAME/KEY: misc_feature
<222> LOCATION: (1)..(1)
<223> OTHER INFORMATION: 5' FAM modification

<400> SEQUENCE: 4
uaaggcuaug aagagauacu u                                          21

<210> SEQ ID NO 5
<211> LENGTH: 23
<212> TYPE: RNA
<213> ORGANISM: Artificial Sequence
<220> FEATURE:
<223> OTHER INFORMATION: siRNA sequence for GAPDH, shown 5' to 3'

<400> SEQUENCE: 5
gacguaaacg gccacaaguu cuu                                        23

<210> SEQ ID NO 6
<211> LENGTH: 23
<212> TYPE: RNA
<213> ORGANISM: Artificial Sequence
<220> FEATURE:
<223> OTHER INFORMATION: siRNA sequence for GAPDH, shown 5' to 3'

<400> SEQUENCE: 6
gaacuugugg ccguuuacgu cuu                                        23

<210> SEQ ID NO 7
<211> LENGTH: 23
<212> TYPE: RNA
<213> ORGANISM: Artificial Sequence
<220> FEATURE:
<223> OTHER INFORMATION: siRNA sequence for GAPDH - shown 5' to 3'
```

```
<400> SEQUENCE: 7
gugugaacca cgagaaauau uuu                                            23

<210> SEQ ID NO 8
<211> LENGTH: 23
<212> TYPE: RNA
<213> ORGANISM: Artificial Sequence
<220> FEATURE:
<223> OTHER INFORMATION: siRNA sequence for GAPDH, shown 5' to 3'

<400> SEQUENCE: 8
aauauuucuc gugguucaca cuu                                            23

<210> SEQ ID NO 9
<211> LENGTH: 21
<212> TYPE: RNA
<213> ORGANISM: Artificial Sequence
<220> FEATURE:
<223> OTHER INFORMATION: siRNA sequence for elastase, shown 5' to 3'

<400> SEQUENCE: 9
ucacuuacag gaucuagaau u                                              21

<210> SEQ ID NO 10
<211> LENGTH: 21
<212> TYPE: RNA
<213> ORGANISM: Artificial Sequence
<220> FEATURE:
<223> OTHER INFORMATION: siRNA sequence for elastase, shown 5' to 3'

<400> SEQUENCE: 10
uuauagaucc uguaagugau u                                              21

<210> SEQ ID NO 11
<211> LENGTH: 21
<212> TYPE: RNA
<213> ORGANISM: Artificial Sequence
<220> FEATURE:
<223> OTHER INFORMATION: non-silencing siRNA control sequence, shown 5'
      to 3'

<400> SEQUENCE: 11
uaaggcuaug aagagauacu u                                              21

<210> SEQ ID NO 12
<211> LENGTH: 21
<212> TYPE: RNA
<213> ORGANISM: Artificial Sequence
<220> FEATURE:
<223> OTHER INFORMATION: non-silencing siRNA control sequence, shown 5'
      to 3'

<400> SEQUENCE: 12
guaucucuuc auagccuuau u                                              21
```